United States Patent
Sobol et al.

(10) Patent No.: US 9,125,677 B2
(45) Date of Patent: Sep. 8, 2015

(54) DIAGNOSTIC AND FEEDBACK CONTROL SYSTEM FOR EFFICACY AND SAFETY OF LASER APPLICATION FOR TISSUE RESHAPING AND REGENERATION

(75) Inventors: Emil Naumovich Sobol, Moscow (RU); Alexander P. Sviridov, Moscow (RU); Michael M. Gorin, Incline Village, NV (US)

(73) Assignee: Arcuo Medical, Inc., Los Altos, CA (US)

( * ) Notice: Subject to any disclaimer, the term of this patent is extended or adjusted under 35 U.S.C. 154(b) by 492 days.

(21) Appl. No.: 13/011,891

(22) Filed: Jan. 22, 2011

(65) Prior Publication Data

US 2012/0191021 A1  Jul. 26, 2012

(51) Int. Cl.
*A61N 5/06* (2006.01)
*A61B 18/20* (2006.01)
*A61B 18/00* (2006.01)

(52) U.S. Cl.
CPC ...... *A61B 18/201* (2013.01); *A61B 2018/00648* (2013.01); *A61B 2018/00732* (2013.01); *A61B 2018/00791* (2013.01)

(58) Field of Classification Search
CPC .............................................. A61N 2005/067
USPC .............. 606/2, 3, 10–16; 607/88–90, 92, 93
See application file for complete search history.

(56) References Cited

U.S. PATENT DOCUMENTS

| | | | |
|---|---|---|---|
| 4,718,417 A | | 1/1988 | Kittrell et al. |
| 4,785,805 A | * | 11/1988 | Joffe et al. ...................... 606/15 |
| 4,973,848 A | | 11/1990 | Kolobanov et al. |
| 4,981,138 A | * | 1/1991 | Deckelbaum et al. ........ 600/477 |
| 5,147,349 A | * | 9/1992 | Johnson et al. ................... 606/4 |
| 5,269,778 A | | 12/1993 | Rink et al. |
| 5,304,173 A | | 4/1994 | Kittrell et al. |
| 5,413,555 A | * | 5/1995 | McMahan .......................... 606/4 |

(Continued)

FOREIGN PATENT DOCUMENTS

| | | |
|---|---|---|
| DE | 19916653 A1 | 10/2000 |
| EA | 009501 B1 | 2/2008 |

(Continued)

OTHER PUBLICATIONS

"Feedback-Controlled Laser Mediated Cartilage Reshaping" Wong et al. Arch. Facial Plast. Surg. vol. 1 pp. 282-287 (1999) in light of US 6,724,958 German et al. (2004).*

(Continued)

*Primary Examiner* — William Thomson
*Assistant Examiner* — John R Downey
(74) *Attorney, Agent, or Firm* — Fenwick & West LLP

(57) ABSTRACT

The efficacy and safety of laser medical treatments are ensured by performing a combination of measurement techniques to examine tissue properties in order to control characteristics of the laser treatments of cartilaginous tissues. In some aspects, a treatment tool is provided that is capable of taking and providing feedback relating to multiple measurements, including temperature measurements (in particular, radiometry), mechanical measurements, light scattering, speckle interferometry, optoacoustic measurements, and monitoring tissue electrical characteristics. The device is capable of providing feedback during the course of laser treatment of tissue to increase the safety and efficacy of treatment.

27 Claims, 11 Drawing Sheets

(56) References Cited

U.S. PATENT DOCUMENTS

| | | | |
|---|---|---|---|
| 5,476,461 A * | 12/1995 | Cho et al. | 606/15 |
| 5,591,157 A | 1/1997 | Hennings et al. | |
| 6,162,787 A | 12/2000 | Sorgente et al. | |
| 6,296,608 B1 * | 10/2001 | Daniels et al. | 600/104 |
| 6,458,120 B1 * | 10/2002 | Shen et al. | 606/10 |
| 6,503,269 B2 | 1/2003 | Nield et al. | |
| 6,542,767 B1 | 4/2003 | McNichols et al. | |
| 6,589,235 B2 | 7/2003 | Wong et al. | |
| 6,724,958 B1 * | 4/2004 | German et al. | 385/33 |
| 7,105,749 B2 * | 9/2006 | Belli et al. | 174/110 R |
| 7,656,923 B2 * | 2/2010 | Di Sessa et al. | 372/50.121 |
| 7,980,745 B2 * | 7/2011 | Shanbaky | 362/581 |
| 8,277,442 B2 * | 10/2012 | Di Sessa et al. | 606/1 |
| 8,448,644 B2 * | 5/2013 | Hennings et al. | 128/898 |
| 8,535,298 B1 * | 9/2013 | Neev | 606/7 |
| 2002/0045811 A1 * | 4/2002 | Kittrell et al. | 600/407 |
| 2002/0045890 A1 | 4/2002 | Celliers et al. | |
| 2003/0036751 A1 | 2/2003 | Anderson et al. | |
| 2003/0138378 A1 * | 7/2003 | Hashimshony | 424/9.6 |
| 2004/0127895 A1 | 7/2004 | Flock et al. | |
| 2005/0119643 A1 * | 6/2005 | Sobol et al. | 606/9 |
| 2005/0259933 A1 * | 11/2005 | Temelkuran et al. | 385/123 |
| 2006/0122668 A1 * | 6/2006 | Anderson et al. | 607/88 |
| 2007/0027443 A1 * | 2/2007 | Rose et al. | 606/16 |
| 2007/0213696 A1 * | 9/2007 | Altshuler et al. | 606/9 |
| 2007/0213698 A1 * | 9/2007 | Altshuler et al. | 606/12 |
| 2007/0239232 A1 * | 10/2007 | Kurtz et al. | 607/87 |
| 2007/0264625 A1 * | 11/2007 | DeBenedictis et al. | 435/4 |
| 2008/0058783 A1 * | 3/2008 | Altshuler et al. | 606/9 |
| 2008/0091249 A1 * | 4/2008 | Wang | 607/88 |
| 2008/0183080 A1 * | 7/2008 | Abraham | 600/466 |
| 2008/0221647 A1 * | 9/2008 | Chamberland et al. | 607/88 |
| 2009/0056044 A1 * | 3/2009 | Rizoiu et al. | 15/22.1 |
| 2009/0076488 A1 * | 3/2009 | Welches et al. | 606/14 |
| 2011/0313299 A1 | 12/2011 | Brennan, III | |

FOREIGN PATENT DOCUMENTS

| | | |
|---|---|---|
| EP | 1279374 A1 | 1/2003 |
| JP | 61-257638 A | 11/1986 |
| JP | 01-135371 | 5/1989 |
| JP | 01-250271 | 10/1989 |
| JP | 06-509952 A | 11/1994 |
| RU | 94007805 A1 | 5/1996 |
| RU | 2114569 | 7/1998 |
| RU | 2138192 C1 | 9/1999 |
| RU | 2196623 C2 | 1/2003 |
| RU | 2224474 C2 | 2/2004 |
| RU | 2422114 | 4/2004 |
| SU | 525042 A | 8/1976 |
| WO | WO 97/39690 | 10/1997 |
| WO | WO 98/55035 | 12/1998 |
| WO | WO 01/22863 A2 | 5/2001 |
| WO | WO 02/32335 | 4/2002 |

OTHER PUBLICATIONS

"Measurement of Radiometric Surface Temperature and integrated Backscattered Light Intensity During Feedback Controlled Laser assisted Cartilage Reshaping" Wong et al. Lasers Med Sci, vol. 13, pp. 68-72 (1998).*

Sobol, E. et al., "Feedback Controlled Laser System for Safe and Efficient Reshaping of Nasal Cartilage" Proceedings of SPIE, 2010, p. 7548-7553.

Sobol, E. et al., "Laser Engineering of Spine Discs," Laser Physics, 2009, pp. 825-835, vol. 19, No. 4.

Sobol, E. et al, "Nasal Septal Cartilage Reshaping, Using an Erbium Doped Glass Fiber Laser" ENT News, 2008, pp. 57-59, vol. 16, No. 6.

Sobol, E. et al., "Optical Methods for Diagnostics and Feed-back Control in Laser-Induced Regeneration of Spine Disc and Joint Cartilages", Proceedings of SPIE, Mar. 2011, 8 pages.

Sobol, E. et al., "Regeneration of Spine Disc and Joint Cartilages under Temporal and Space Modulated Laser Radiation," Proceedings of SPIE, 2009, p. 7190B1-7190B7.

Wong, B. et al., "Feedback Controlled Laser-Mediated Cartilage Reshaping," Arch Facial Plast Surg, Oct.-Dec. 1999, pp. 282-287, vol. 1.

Wong, B.J.F. et al., "Measurement of Radiometric Surface Temperature and Integrated Backscattered Light Intensity During Feedback-Controlled Laser-Assisted Cartilage Reshaping," Lasers in Medical Science, 1998, pp. 66-72, vol. 13.

Bagratashvili, V.N., et al., Acoustic Control of Laser Shaping of Cartilage. In: Laser Spectrometry and Optical Diagnostics: Novel Trends and Applications in Laser Chemistry, Biophysics, and Biomedicine, ICONO'98, 1999, vol. 3732, Ch.49, p. 312-319.

Bagratashvili et al Kinetics of water transfer and stress relaxation in cartilage heated with 1.56 micron fiber laser; Proceedings of SPIE vol. 3914; (2000); pp. 102-107.

Bagratashvili, V.N., et al., "Thermal and diffusion processes in laser-induced stress relaxation and reshaping of cartilage," Journal of Biomechanics, 1997, vol. 30, 8, pp. 813-817.

Chew, C., et al., "Feedback-controlled cartilage reshaping with an Nd:YAG laser: effects of pH variation," Proc. SPIE, 1998, V.3245, pp. 206-216.

Choy, D.S.Y. et al.,"Percutaneous Laser Disc Decompression, a New Therapeutic Modality", Spine, 1992, pp. 949-956, vol. 17, No. 8.

Choy, D. et al., "Percutaneous Laser Nucleolysis of Lumbar Disks", New England Journal of Medicine, 1987, pp. 771-772, vol. 317, No. 12.

Helidonis, E.M., et al., "The histology of laser thermo-chondroplasty," American Journal of Otolaryngology, Nov.-Dec. 1994, vol. 15, No. 6, pp. 423-428.

Helidonis, E.M., et al., "Laser shaping of composite cartilage grafts," American Journal of Otolaryngology, 1993, vol. 14, No. 6, p. 410-412.

Helidonis, E.M., et al., Shaping of Nasal Septal Cartilage with the Carbon Dioxide Laser—Preliminary Report of Experimental Study. Lasers in Medical Science, 1994, vol. 9, pp. 51-54.

Jones, N., et al., "A prospective randomized study of laser reshaping of cartilage in-vivo", Lasers in Medical Sciences, 2001, vol. 16, No. 4, p. 284-290.

Ovchinnikov, Y., et al., "Laser Septochondrocorrection," Surgical Technique, ARCH Facial SURG, Jul.-Sep. 2002, pp. 180-185, vol. 4.

Ovchinnokov, Y., et al., Arbitrary reshaping of cartilage under laser radiation, (in Russian) Annals of Otolaryngology, 1995, 3, pp. 5-10 (With English Summary).

Ovchinnokov, Y., et al., "Application of surgical lasers for arbitrary forming of cartilaginous tissue in otolaryngology (in Russian) Annals of Otolaryngology," 1996, 3, 21-22 (With English Summary).

Ovchinnokov, Y., et al., "Non-invasive correction of nasal septum—laser surgery opportunity," The Doctor, 1999, No. 12, pp. 35-36. (With English Summary).

Omel'Chenko, A., et al., "Mechanical examination of cartilage reshaped under laser radiation," Advance Materials, 1999, vol. 3, p. 56-63.

Sobol, E., et al., "Calculation of the kinetics of heating and structural changes in the cartilaginous tissue under the action of laser radiation," Quantum Electronics 1998, V.28, N. 7, p. 633-636.

Sobol, E., et al., "Heating and structural alterations in cartilage under laser radiation," IEEE Journal of Quantum Electronics, Apr. 1999, V.35, N. 4, pp. 532-539.

Sobol, E., et al., "Laser Reshaping of Cartilage," Biotechnology and Genetic Engineering Reviews, Aug. 2000, pp. 539-564, vol. 17.

Sobol, E., et al., "Laser shaping of Cartilage," Proceedings of Laser Surgery: Advanced Characterization, Therapeutics, and Systems IV, Maiman Award paper at the Symposium on Biomedical Optics (Los Angeles, Jan. 22-25, 1994), SPIE—The international society for optical engineering, 1994, pp. 43-49, vol. 2128.

Sobol, E., et al., Mechanism of laser-induced stress relaxation in cartilage, Proc SPIE, 1997, vol. 2975, p. 310-315.

Sobol, E., "Phase Transformations and Ablation in Laser-Treated Solids," pp. 316-322, John Wiley & Sons Inc., New York, 1995.

Sobol, E., "Phase Transformations and Ablation in Laser-Treated Solids," John Wiley & Sons Inc., New York, 1995.

(56) References Cited

OTHER PUBLICATIONS

Sobol, E., et al., "Phenomenon of cartilage shaping using moderate laser heating," Proc. SPIE, 1996, vol. 2623, p. 548-552.
Sobol, E., et al., "Stress relaxation and cartilage shaping under the moderate laser radiation," Optical Engineering bulletin, 1994, 3, 26-28.
Sobol, E., et al., "Stress relaxation and cartilage shaping under laser radiation," Proc. SPIE, 1996, vol. 2681, p. 358-363.
Sobol, E., et al., "Study of cartilage reshaping with a Holmium laser," Proc SPIE, 1996, vol. 2623, p. 544-547.
Sobol, E., et al., "Theoretical Modeling of Heating and Structure Alterations in Cartilage under Laser Radiation with Regard of Water Evaporation and Diffusion Dominance," Proc SPIE, 1998, V.3254, p. 54-63.
Sobol, E., et al., "Thermal processes and water diffusion in cartilaginous tissue under laser radiation," Proc. of Minsk International Forum on Heat and Mass Transfer, Minsk, 1996, vol. 7, 205-208. (With English Summary).
Sviridov, A., et al., "Dynamics of Optical and Mechanical Properties of Cartilage under Laser Heating," Proc. SPIE, 1997, V.2923, pp. 114-117.
Sviridov, A., et al., "Effect of Holmium laser radiation on stress, temperature and structure alterations in cartilage," Lasers in Medical Science, 1998, vol. 13, pp. 73-77.
Tomilova, L., "Synthesis of new sulfonated mono-and diphthalocyanines d and f elements and perspectives of their application for plastic surgery," Proc. SPIE, 1996, vol. 2623, p. 62-65.
Velegrakis, G., et al., "Thermochondroplasty of Rabbit Ear Cartilage using the Carbon Dioxide Laser," Lasers in Medical Science, 1994, p. 265-272, vol. 9.
Velegrakis, G.A., et al., "In Vitro Ear Cartilage Shaping With Carbon Dioxide Laser," Ann. Otol. Rhino. Laryngol., 2000, vol. 109, p. 1162-1166.
Wang, Z., et al., "Endoscopic Laser-assisted reshaping of collapsed tracheal cartilage," A laboratory study, Annals of Otology, Rhinology and Laryngology, 1996, vol. 105, pp. 176-181.
Wang, Z., et al., "Laser-assisted cartilage reshaping: in vitro and in vivo animal studies," Society of Photo-Optical Instrumentation Engineers. Proceedings 2395, 296-302, (1995).
Wong, B.J., et al., "Characterization of Temperature Dependent Biophysical Properties During Laser Mediated Cartilage Reshaping," IEEE Journal of Selected Topics in Quantum Electronics, 1999, V.5, p. 1095-1102.
Wong, B.J., et al., "Critical temperature transitions in laser-mediated cartilage reshaping," Proc. SPIE, 1998, vol. 3245, p. 161-172.
Wong, B.J., et al., "Stress Relaxation of Porcine Septal Cartilage During Nd:YAG ($\lambda$= 1.32 µm) Laser Irradiation: Mechanical, Optical, and Thermal Responses," Journal of Biomedical Optics, 1998, vol. 3, Issue 4, p. 409-414.
Wong, B.J., et al., "Thermo-Optical Response of Cartilage during Feedback Controlled Laser-Assisted Reshaping," Proc SPIE, 1977, V.2970, p. 380-391.
PCT International Search Report and Written Opinion, PCT/RU2004/000454, Feb. 17, 2007, 12 Pages.
European Communication for European Patent Application No. EP 04816151.7, Jan. 21, 2010, 7 Pages.
Supplementary Partial European Search Report for European Patent Application No. EP 04816151.7, Sep. 16, 2009, 7 Pages.
Examiner's first report on Australia patent application No. 2004271876, Jun. 25, 2009, 2 Pages.
Office Action for Mexican patent application No. PA/a/2005/009981 Oct. 28, 2009, 7 pages.
Examiner's Office Letter for Japan Patent Application No. 2006-526848, Apr. 12, 2010, 3 pages.
PCT International Search Report and Written Opinion, PCT Application No. PCT/US2012/021842, May 23, 2012, 13 pages.
Australian Second Examination Report, Australian Application No. 2004271876, Nov. 15, 2010, 2 pages.
European Examination Report, European Application No. 04816151.7, Mar. 30, 2011, 6 pages.
European Examination Report, European Application No. 04816151.7, Aug. 27, 2010, 5 pages.
Indian Examination Report, Indian Application No. 4383/DELNP/2005, Jan. 7, 2011, 2 pages.
United States Office Action, U.S. Appl. No. 13/011,890, May 27, 2014, 9 pages.
United States Office Action, U.S. Appl. No. 13/011,890, Sep. 10, 2014, 7 pages.
United States Office Action, U.S. Appl. No. 10/942,981, May 22, 2014, 7 pages.
United States Office Action, U.S. Appl. No. 10/942,981, Jan. 16, 2014, 8 pages.
United States Office Action, U.S. Appl. No. 10/942,981, Dec. 27, 2010, 6 pages.
United States Supplemental Office Action, U.S. Appl. No. 10/942,981, Feb. 23, 2010, 8 pages.
United States Office Action, U.S. Appl. No. 10/942,981, Dec. 14, 2009, 7 pages.
United States Office Action, U.S. Appl. No. 10/942,981, Apr. 15, 2009, 6 pages.
United States Office Action, U.S. Appl. No. 10/942,981, Jul. 1, 2008, 8 pages.
United States Office Action, U.S. Appl. No. 10/942,981, Jan. 16, 2015, 7 pages.

* cited by examiner

900

A-A

1000

A-A

1100

DIAGNOSTIC AND FEEDBACK CONTROL SYSTEM FOR EFFICACY AND SAFETY OF LASER APPLICATION FOR TISSUE RESHAPING AND REGENERATION

FIELD

The present disclosure relates to laser medical treatments, and specifically to diagnostic and feedback control systems for laser medical treatments.

BACKGROUND

Non-destructive laser heating has a variety of applications in the field of medicine, including the alteration of tissue stress and structure for cartilage reshaping in otolaryngology and for the activation of reparative processes in joints and spine discs in orthopedics and spine surgery. Existing approaches suffer from significant limitations as a result of overheating of the tissue joining the ablation zone and the undesirable effect on surrounding tissues, which manifest as scarring and/or increased probability of relapse.

The limitations of the existing technologies are associated with difficulties in controlling the modification processes of the tissue structure and the mechanical properties of the tissue. For example, one particularly difficult aspect for nasal septum reshaping is the selection of the optimal treatment site. The area of laser application should ideally be determined according to the initial septum shape and the distribution of initial stress in the tissue, however, these properties vary widely among patients and across a given tissue area. Using existing methods, laser radiation is applied along a bent line, which diminishes efficacy and limits the number of septum deviation types that can be corrected.

Similar issues arise for laser regeneration of disks (LRD). Since the optical properties of the tissue are also individual and depend on the tissue age and condition, in particular the water content, the initial choice of the laser settings and any adjustments to be made to the laser settings in the course of LRD are not systematically selectable using existing methods. In this case, the safety of the laser treatment is defined by the breadth of the therapeutic window, and the initial laser settings are chosen near the lower boundary of the therapeutic window (i.e., in the range of safe laser settings). Thus, there is only a narrow range of laser conditions that are both efficacious and non-destructive to tissues, and existing methods fail to provide adequate guidance regarding the selection of initial laser settings.

During laser irradiation of tissue, the treated area undergoes a number of changes, including without limitation: changes in temperature, porosity, absorptivity, residual stress across an area of tissue, and the like. While methods exist for independently measuring changes in certain individual properties, no known method exists that is capable of comprehensively measuring these characteristics and integrating them for use in a feedback system. Moreover, no known method exists that enables the use of these measurements as feedback to improve the efficacy and safety of the laser treatment of tissue. Existing methods are incapable of providing guidance regarding initial laser settings, including optimized selection of the treatment site. Existing methods also fail to provide real-time measurement of a combination of tissue condition parameters that enable the customization of treatment conditions for improved efficacy and safety.

Therefore, a need exists in the art for improved methods and tools that are responsive to a number of parameters as measured during the course of laser tissue treatment and are capable of taking into account a variety of factors affecting the efficacy and safety of non-destructive laser heating treatments.

SUMMARY

The present disclosure provides improved diagnostic and feedback systems that advantageously enable a practitioner to simultaneously measure a plurality of tissue conditions and to use those measurements via a feedback system to customize non-destructive laser heating treatments.

In various aspects, the present disclosure provides a device for laser treatment of cartilaginous tissues. In various aspects, the device is made up of a cylinder having a lumen; a first fiber optic system passing through the lumen of the cylinder; a first laser emitting a first beam of laser light having a wavelength, power, pattern, and pulse profile sufficient to produce a non-destructive, irreversible modification of a cartilaginous tissue, wherein the laser is positioned at the proximal end of the cylinder, and wherein the first beam of laser light passes through the first fiber optic system; a plurality of sensors, wherein each sensor is independently capable of measuring a physical or chemical characteristic of the cartilaginous tissue during application of a first laser beam; a feedback control system connected to the plurality of sensors, wherein the feedback control system is capable of analyzing the measurements of the plurality of sensors, identifying optimal outputs for the first laser, and providing feedback regarding optimal outputs to the laser control unit; and a laser control unit that controls the first laser, wherein the laser control unit causes the first laser to emit a first laser beam, wherein the properties of the first laser beam approximate the optimal outputs identified by the feedback control system.

In some aspects, the device also contains a second fiber optic system passing through the lumen of the cylinder; a second laser emitting a second beam of laser light having a wavelength, power, pattern, and pulse profile sufficient to induce a non-destructive effect in the cartilaginous tissue that is measureable and correlates with cartilaginous tissue characteristics, wherein the second laser is positioned at the proximal end of the cylinder, and wherein the second beam of laser light passes through the second fiber optic system; and wherein one of the sensors is a light sensor capable of measuring the cartilaginous tissue characteristic induced by the second beam of laser light.

In various other aspects, the device can assume any number of configurations in order to provide safe and efficacious laser treatment using a feedback controlled system. The configuration can be adjusted to suit the particular therapeutic method, for example, the types of sensors used and orientation of the device can be optimized for a given therapeutic method. Therapeutic methods according to the present disclosure include, without limitation: laser regeneration, laser reshaping, laser regeneration of joint cartilage, and laser reshaping of throat cartilage. The particular combination of sensors used can be optimally determined based on which of these therapeutic methods is being used.

The present device advantageously provides novel component configurations and locking mechanisms that enable integration of the working laser radiation and the diagnostic mechanism in the same device. The system enables real-time feedback regarding output settings prior to and during treatment. Also envisioned are systems for the release of drugs into tissues and enhanced treatment through the incorporation of oscillators into the systems.

BRIEF DESCRIPTION OF THE DRAWINGS

FIG. 7A illustrates a longitudinal view of a hollow body. FIG. 7B illustrates a side view of a hollow body. FIG. 7C illustrates a clipping mount for fixation of a hollow body in combination with a clipping mount.

DETAILED DESCRIPTION

Overview of Tissue Measurements

Figure 1:
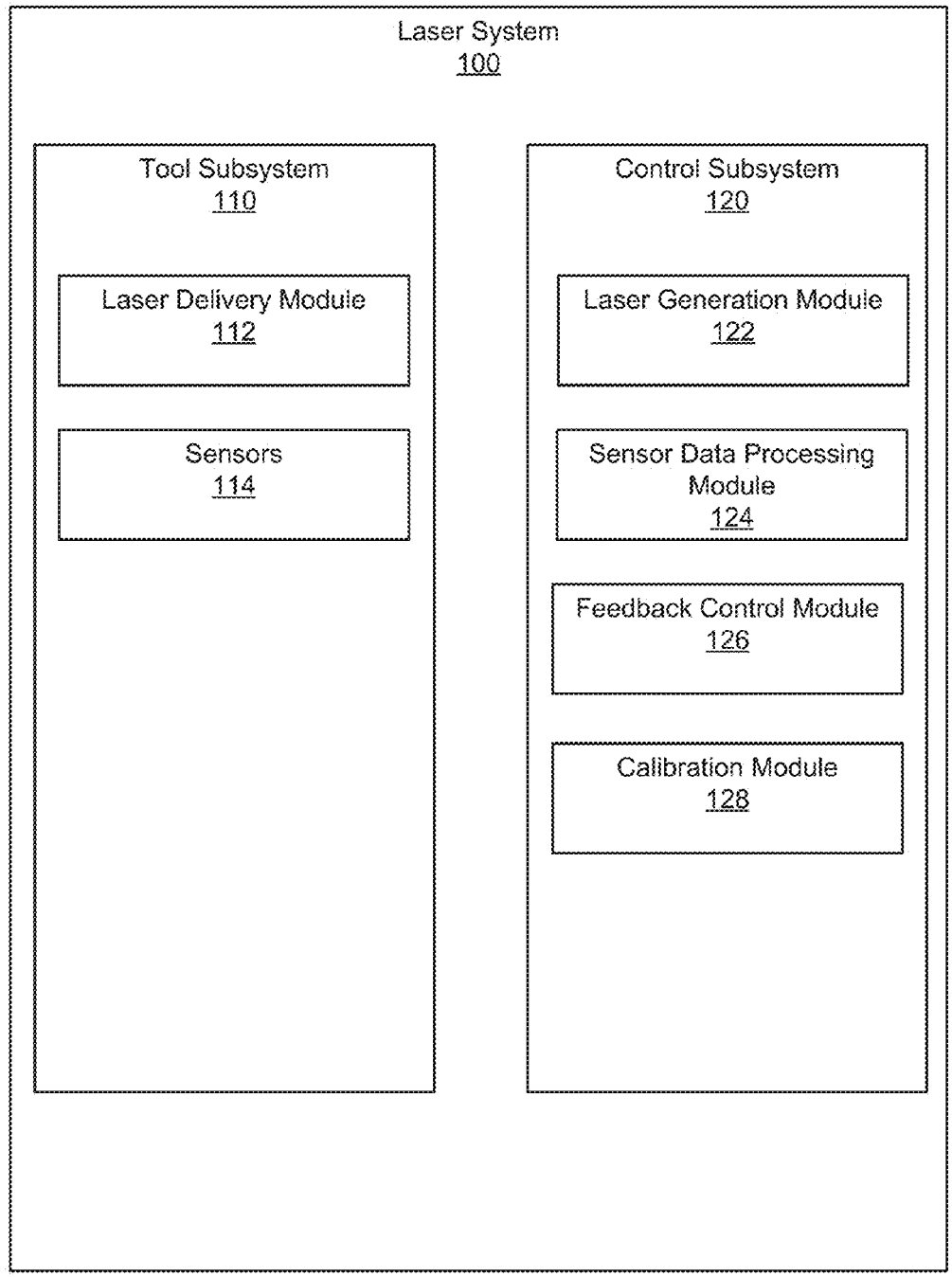
FIG. 1 illustrates a high level block diagram of a laser system, in accordance with an aspect.

Various aspects of the invention ensure the efficacy and safety of laser medical treatments based on controllable alterations in tissue structure and stress field. A combination of measurement techniques is used to obtain a grounded selection of the laser application area, a grounded choice of initial laser and mechanical settings, the correction of characteristics of exposure in the course of treatment, and/or the prediction of the results of treatment and the necessity of a repeated treatment. A combination of measurement techniques is advantageous because each of the individual available techniques (optical, mechanical, electrical, etc.) which can be used to examine tissue properties does not allow a practitioner to obtain a result with a interpretation having a single meaning, because the result of any single measurement technique depends on a number of parameters such as temperature, distribution of light scattering elements, water content and movement. The information needed for reliable action can be obtained only using a specific combination of the diagnostic methods described below.

The present disclosure contemplates the combination of any suitable tissue state measurements that enhances the efficacy and safety of laser medical treatments. In various aspects, measurements corresponding to temperature, deformation, and stress are obtained. Exemplary measurements include, without limitation: temperature measurements, light scattering measurements, speckle interferometry measurements, optoacoustic measurements, electrical measurements, modulated differential scanning calorimetry measurements, and the like. The present disclosure contemplates the use of any variety of configurations and sensors 114 that facilitate making those measurements.

Temperature measurements can be obtained using any suitable sensor, including without limitation: thermocouples, thermistors, IR radiometers, electrical impedance tools, photoacoustics tools, proton resonance frequency tools, IR spectrometers (e.g., Fourier transform IR spectrometers), and the like. Temperature measurement of laser-treated tissue, for example, radiometry measurement, enables a practitioner to determine tissue temperature, which in turn allows the practitioner to approach and avoid the threshold temperature above which tissue damage occurs. Dynamic temperature measurement enables a practitioner to determine tissue absorptivity, to establish the presence of irreversible alterations in tissue structure (i.e., tissue denaturation), and to estimate tissue water content. In one aspect, water content is estimated through the use of two laser beams having similar wavelengths for diagnostic measurements.

Light scattering measurement of laser-treated tissue enables a practitioner to characterize pore structure in the tissue matrix. Light scattering measurement also enables the practitioner to characterize the cavitations processes, which arises, for example, in the nucleus pulposus under laser radiation.

Speckle interferometry measurement of laser-treated tissue enables a practitioner to diagnose micro-deformation in the tissue matrix and to characterize water transport through tissue. Speckle interferometry measurement can be performed in combination with radiometric measurements to identify the threshold of tissue denaturation.

Optoacoustic measurement of laser-treated tissue enables a practitioner to identify tissue absorptivity and alterations in tissue mechanical properties in the course of laser irradiation.

Electrical measurement of laser-treated tissue enables a practitioner to estimate the degree of the maturity of the tissue pore system and to identify the presence of tissue discontinuities.

Example characteristic parameters of the object in the prospective area of laser treatment that can be determined by the system described herein include: tissue absorptivity and tissue mechanical properties.

Tissue absorptivity measurements can be obtained using any suitable sensor, including without limitation: radiometry, optoacoustic measurements, or the like.

Tissue mechanical properties, in particular, effective elastic modulus and mechanical stress distribution, can be obtained using any suitable means, including without limitation: optoacoustic, multi-sectional pneumatic system with pressure sensor measurements, or the like.

Example characteristic parameters of the tissue that can be controlled in the course of laser treatment by the system described herein include without limitation: structural alterations (e.g., pore presence and size), water concentration distribution, and denaturation zone presence, which can be measured with light scattering, radiometry, and speckle interferometry techniques. Temperature field in the laser-heated area of the object can also be measured to characterize tissue properties during treatment.

Deformation measurements can be obtained using any suitable sensor, including without limitation: light scattering tools, speckle interferometers, OCTs, other tomography techniques including photoacoustic tomography or thermoacoustic tomography, and the like.

Stress measurements can be obtained using any suitable sensor, including without limitation: mechanical loading tools, piezoelectric film tools, tensiometers, or the like. Alternatively, stress can be calculated using data from deformation measurements.

The controlled characteristics of the object, in particular, temperature and its spatial distribution, are mediated with the signals measured by the system described herein. For example, such signals can be an integral intensity of thermal radiation depending on the temperature and the geometrical and physical characteristics of the measuring system. The values of the controlled parameters and their characteristic alterations during laser heating can be determined empirically on the basis of preliminary experiments using tissue phantoms with regard of geometrical and physical characteristic of the measuring system. In many cases, the controlled characteristics can be determined using theoretical models describing the controlled characteristics as the functions on the characteristic parameters of the object.

System Configuration

FIG. 1 illustrates a high level block diagram of a laser system 100 in accordance with an aspect. The laser system 100 includes a tool subsystem 110 and a control subsystem 120.

The tool subsystem 110 delivers the laser medical treatment to the treatment site and records measurements of tissue properties, for example, before, during, and after laser medical treatment. The tool subsystem 110 includes a laser delivery module 112 and one or more sensors 114.

The sensors 114 include various types of sensors, depending on the combination of measurement techniques used for the application of the laser system 100. The sensors 114 can include any combination of temperature sensors, optical sensors for light scattering measurements or interferometric measurements, mechanical sensors, optoacoustic sensors, and electrical sensors. In some aspects, sensors 114 are attached to a handheld tool in proximity to the treatment site. In other aspects, sensors 114 can be part of or reside inside of a housing of the laser delivery module 112 which can be inserted into the tissue at the treatment site. In still other aspects, sensors 114 can be positioned at a remote location from the laser delivery module 112. The sensors 114 collect data relevant to measurement of the environment for treatment for use in obtaining a grounded selection of the laser application area, a grounded choice of initial laser and mechanical settings, the correction of characteristics of exposure in the course of treatment, and/or the prediction of the results of treatment and the necessity of a repeated treatment.

The control subsystem 120 controls the operational parameters of the laser system 100. As illustrated in the aspect of FIG. 1, the control subsystem 120 includes a laser generation module 122, a sensor data processing module 124, a feedback control module 126, and a calibration module 128.

In some aspects, the laser delivery module 112 includes an optical fiber through which laser radiation is delivered. The laser delivery module 112 receives the laser radiation from the control subsystem 120, as will be described in greater detail below. In one aspect, the laser delivery module 112 delivers laser radiation for short-term (e.g., time periods of a few seconds) laser heating of the tissue under the stress relaxation threshold. Namely, the temperature of the tissue being heated has a value lower than $T_1$ where $T_1$ is the temperature for stress relaxation due to non-reversible alterations in tissue structure. The value of $T_1$ depends on tissue type and other relevant conditions. In one embodiment, for cartilages, $T_1$=65-75° C.; for cornea $T_1$=45-55° C.

The laser generation module 122 controls the operation of the laser, including for example, whether the laser is switched on or off; the frequency, length or pattern of laser pulses; the laser wavelength; the laser power; the laser intensity; the laser spot diameter, the treatment pattern, and/or any other controllable parameter of the laser. The laser generation module 122 transmits the laser radiation to the laser delivery module 112 of the tool subsystem 110.

In various aspects, the laser generation module 122 can determine the wavelength of laser power according to the desired light penetration. For example, light penetration depth in healthy cartilage is approximately 0.8 mm for wavelengths of 1.56 microns, 0.3 mm for wavelengths of 1.45 microns, and 3 mm for wavelengths of 1.32 microns. For degenerated cartilage, penetration depth can be higher at these wavelengths. As further examples, for laser reshaping of a nasal septum, for normal nasal septum thickness, the laser wavelength is 1.56 microns; pressing of the mucosa increases penetration depth up to 1.2 mm; and for a thick area of nasal septum a wavelength of 1.32 microns can be used. For laser regeneration of joint cartilage, an initial wavelength can be 1.56 microns. For thinner areas or for degenerated areas where there is less water content and a lower absorption coefficient, the wavelength can be changed to 1.44 microns, for example.

In various aspects, the laser generation module 122 can also determine the pulse length of the laser treatment. For example, the pulse length for laser regeneration can be from 0.1 to 2 seconds, and the pulse length for laser reshaping can be from 0.5 to 5 seconds. Shorter pulse length provides higher mechanical effect with lower average temperature. This can be useful for regeneration, especially for highly degenerated cartilage. In various aspects, the sensors 114 are capable of detecting degenerated tissue. If the sensors 114 detect a more degenerated area, it will be useful to decrease pulse duration (for LRD—from 1 to 0.3 seconds, for laser regeneration of joint cartilage—from 0.5 to 0.2 seconds). Accordingly, laser power can be also corrected to keep temperature at the optimal level. An increase of laser pulse duration (i.e., exposure time) will provide more homogeneous heating which can be useful to reshape thicker cartilage or areas were stress in the middle of the nasal septum is higher than average stress in the middle of the septum. In these areas of higher stress, pulse length can be increased, for example, from 0.7 to 1.5 seconds.

In various aspects, the laser generation module 122 can also determine the spot diameter. For example, the spot diameter can be from 0.2 to 2 mm for regeneration, and from 0.5 to 5 mm for reshaping.

In various aspects, the laser generation module 122 can also determine the treatment pattern. Examples of suitable predefined treatment patterns include, without limitation, a circular pattern, elliptical pattern, donut pattern, quadrant pattern, rectangular pattern, arc pattern, annular arc pattern, or the like. Furthermore, a user-defined pattern can be created and stored for later use, and such a user-defined treatment pattern can be used in the same way as any other predefined pattern.

In one aspect, the laser generation module 122 provides a treatment pattern, wherein the treatment pattern is selected in order to account for tissue non-homogeneity and to alternate between treated and untreated areas of the tissue. In this aspect, the spacing can be, for example, from 0.5 to 5 mm. For laser reshaping of cartilage, the treatment pattern can be characterized by two spacing parameters, the first parameter being the separation between the laser spots in a line (e.g., from 1 to 2 mm); and the second parameter being the separation between the treatment lines (e.g., from 2 to 4 mm). These spacing parameters can be adjusted to account for cartilage topography and heterogeneity of stress distribution in the laser-treated zone. For example, when the sensor data shows that heterogeneity of residual stress is high (i.e., the spacing between zones with differing stresses is of approximately 4 mm), the separation between the treatment lines can be decreased from 4 mm to 2 mm. In further aspects, when there is a localized area with high relative stress, the spacing between laser spots can be decreased (from 2 to 1 mm). For laser regeneration of joint cartilage, the separation between the laser spots is typically 1.5 mm. This spacing can be adjusted for thinner cartilage areas or for small damaged or degenerated zones of cartilage to be treated, for example, the spacing between laser spots can be decreased from 1.5 mm to 1.0 mm. For large, relatively homogeneous zones, the spacing between laser spots can be increased, for example, from 1.5 mm to 2.0 mm.

In certain aspects, using the laser generation module 122, optimal or near optimal frequencies of laser pulses can be obtained. It is noted that application of external mechanical stress to cartilage leads to the release of water from the compressed areas. Sodium and calcium ions associated with the water are transported along with the released water. Since sodium ions are smaller than calcium ions, sodium ions have a greater rate of diffusion in solution relative to calcium ions. Lag times in calcium ion transport result in heterogeneous calcium concentrations in the compressed tissues, however, heterogeneity in calcium concentration decreases with time due to mass transfer under a concentration gradient. It is known that calcium is vital to cellular metabolism. (M. J. Berridge, P. Lipp, and M. D. Bootman, "Calcium—a life and death signal," Nature 395, 645-648, 1998).

The release of water under mechanical stress and concomitant transport of sodium and calcium ions are dependent on the spatial and temporal modulation of the laser beam as generated by the laser generation module 122. Specifically, a temperature gradient produced by the application of a laser beam leads to thermo-mechanical stress, which causes water to release at a greater rate, enhances the transport rate of calcium, and minimizes heterogeneity in calcium concentration. Pulsed periodic laser action results in formation of waves of calcium concentration. Increases in calcium transport rates are possible, however, only in certain ranges of laser pulse frequencies. When the laser pulse frequency is too high, calcium ions do not have sufficient time to move significantly and, thus, no concentration gradient arises. At lower laser pulse frequencies, there is sufficient time for calcium diffusion, thereby diminishing the concentration gradient.

Laser heating also leads to the formation of micropores in cartilaginous matrices. These micropores increase water permeability and promote ion movement, thereby shifting the boundary of the frequency region allowing separation of calcium and sodium ions. For these reasons, the use of increased laser pulse frequencies can be beneficial in the course of laser medical treatment of cartilage. In certain aspects, the sensors 114 measure the optical and electrical characteristics of the cartilaginous tissue in the course of laser treatment. The degree of tissue poration can then be determined using the sensor data processing module 124. Through the use of the feedback control module 126, the laser pulse frequency generated by the laser generation module 122 can be adjusted in order to optimize the degree of tissue poration.

The sensor data processing module 124 of the control subsystem 120 receives data collected by the sensors 114. The sensor data is processed to determine, for example, a grounded selection of the laser application area, a grounded choice of initial laser and mechanical settings, the correction of characteristics of exposure in the course of treatment, and/or the prediction of the results of treatment and the necessity of a repeated treatment. The sensor data processing module 124 can output the processed sensor data for display to a practitioner for subsequent action or can convey it to the feedback control module 126.

The feedback control module 126 receives at least some of the processed sensor data from the sensor data processing module 124 as a feedback, for example, for identifying laser settings to communicate to the laser generation module 122. Alternatively or additionally, the feedback control module 126 can use at least some of the processed sensor data to correct the characteristics of exposure in the course of treatment through feedback to the laser generation module 122.

The calibration module 128 is used to calibrate the settings of the laser system 100 prior to use. The calibration module 128 can act as an additional safety check on the operation of the laser system 100 to be within safe limits. In one aspect, calibration of the control subsystem 120 and the sensors 114 can be performed using standardized tissue phantoms. Various prepared phantoms can be used to model different tissue conditions for the choice of the initial laser settings and to establish the sensitivity characteristics of the laser system 100. The tissue phantom can be made from gel comprising a specific concentration of water, which provides light absorptivity and thermal conductivity comparable to those of cartilage or other target tissues. The calibration process can comprise measurement of the spatial distribution of light intensity, which provides both the condition of the laser tool and the optical heterogeneity of the tissue area to be treated.

Method of Operation

Figure 2:
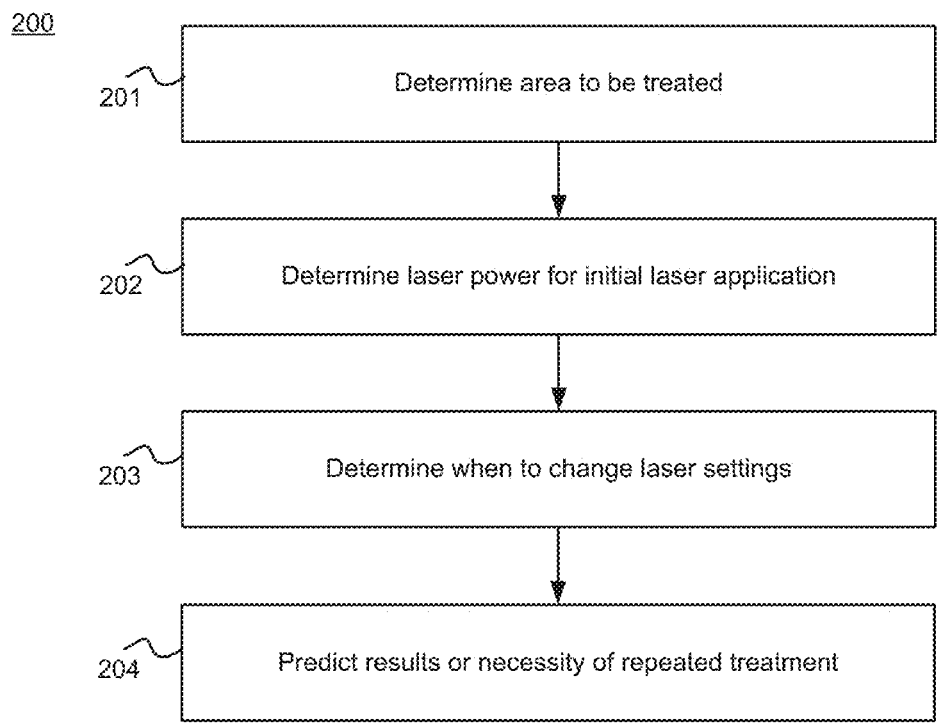
FIG. 2 illustrates a method of operating a laser system, in accordance with an aspect.
Figure 3A:
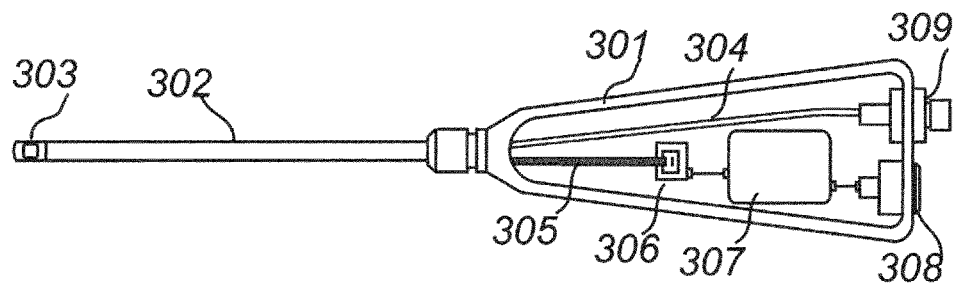
FIGS. 3A-C illustrate a tool for use with the laser system, in accordance with an aspect.
Figure 3B:
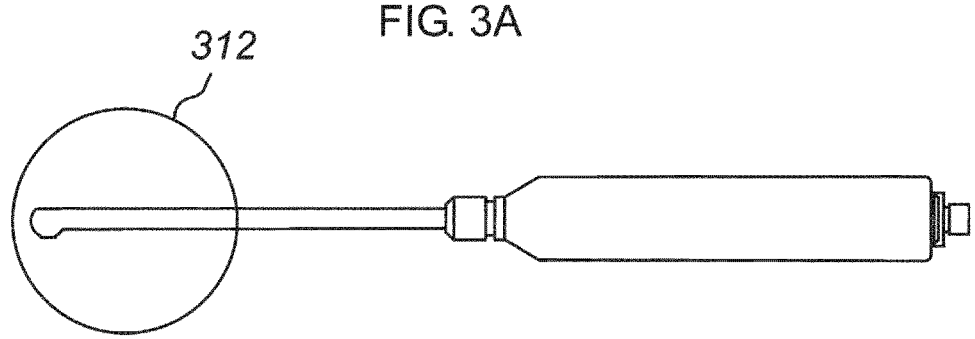
Figure 3C:
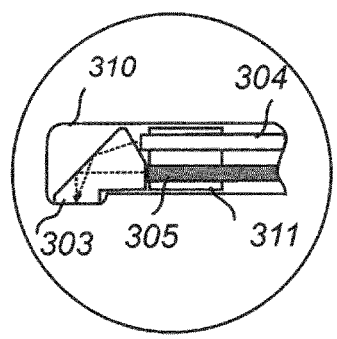

FIG. 2 illustrates a method of operating a laser system 100, in accordance with an aspect of the present disclosure. First, in step 201, the area to be treated is determined, for example, based on the data relating to the spatial distributions of: the tissue, water content, and stress in the tissue as determined using sensors 114. Any suitable method can be used to define the spatial distribution of internal stress in the tissue. Exemplary methods include the use of: (a) optoacoustic signals from varying irradiated tissue zones; (b) a multi-sectional inflatable unit allowing the measurement of the magnitude and spatial distribution of the pressure along the tissue area undergoing to laser treatment; or (c) the like.

Laser treatment is more effective if there is adequate site selection in step 201. For instance, if in the course of determining the area to be treated in step 201 (e.g., for LRD), a significant numbers of pores or calcified inclusions are identified during pre-surgery diagnostics (e.g., with the use of speckle-interferometry and light scattering techniques), it may be advantageous to reposition the area of laser application. For laser septocorrection (LSC), the laser treatment is enhanced if laser application occurs at areas where there are manifested stress concentrator points. In particular, areas of cartilage (and mucosa) of differing thickness can be favorable.

In step 202, the laser power for the initial laser application is determined, for example, based on the data relating to the spatial distribution of the absorptivity of laser radiation. For preliminary diagnostics, a pulse of laser radiation which heats the treatment site slightly without stress relaxation and without non-reversible alterations in tissue structure can be used. Accordingly, the measurement of local temperature in varying tissue zones allows the determination of the spatial distribution of absorptivity. Successive application of laser pulses of two close wavelengths with substantially different light absorptivity (for example 1.56 and 1.45 microns) allows the determination of the spatial distribution of water concentration in the tissue. Any suitable laser power can be used according to the present disclosure, and optimal laser power depends on the particular laser treatment to be performed and the pulse profile and repetition rate used. Exemplary laser powers include: (a) for reshaping of a nasal septum with 1.56 microns radiation using low power (e.g., 0.8 W), medium power (e.g., 1.0 W), or high power (e.g., 1.2 W); (b) for LRD with 1.56 microns radiation (in pulse repetition mode with a pulse duration of 1 second, pulse repetition rate 0.5 Hz, and interval between pulse series of 10 seconds) of at lower power (e.g., 1.0 W), medium power (e.g., 1.2 W), or high power (e.g., 1.4 W); or (c) for laser regeneration of knee joints with 1.45 microns radiation at lower power (e.g., 0.6 W), medium power (e.g., 0.8 W), or high power (e.g., 1.0 W); or (d) for laser reshaping of a cornea with 1.56 microns radiation in pulse repetition mode with pulse duration of 0.5 seconds and pulse repetition rate 1.3 Hz using low power (e.g., 0.5 W), medium power (e.g., 0.6 W), or high power (e.g., 0.7 W).

In step 203, it is determined when to change laser settings based on updated data from the sensors 114, and in particular, it is determined when to switch the laser off. In various aspects, the device can be controlled by a practitioner, automatically by the device using a predefined rule, or by a combination thereof. The decision of when to change the laser settings can be made on the basis of the data relating to the alteration in spatial distribution of the stress, micropores, and/or on the non-reversible alterations in tissue structure. To define the spatial distribution of micropores in the tissue, any suitable measurement or combination of measurements can be used, for example: (a) water permeability measurements; (b) light scattering measurements, in particular, optical coherent tomography; and/or (c) electrical impedance measurements can be used. Methods (a) and (b) above can also be used to identify tissue structural alterations (i.e., tissue denaturation) and to find their spatial distribution in the tissue.

For example, formation of relatively large pores and discontinuity in the nucleus pulposus of a spinal disc (as can be identified with a light scattering technique) can suggest a need to decrease laser power or to switch the laser off. Moreover, an increase of tissue elastic modulus found upon the passage to the next zone in the course of laser treatment of a nasal septum, can suggest a need to modify the treatment tactics (e.g., by modifying the localization and the order of the irradiation zones). Additionally, since the optimal frequencies of laser thermo-mechanical action depend on the velocity of the interstitial fluid transfer, which is determined by the porosity characteristics of the tissue matrix as described herein, the monitoring of the optical and electrical tissue characteristics in the course of LRD allows one to establish the instant when a threshold number of newly arising micropores have been produced. Once that threshold number is reached, the user can then alter the modulation frequency and power of the laser irradiation within a short timeframe.

Optionally, in step 204, the results of the treatment can be predicted, and/or the necessity of a repeated treatment can be determined. For example, the information about residual stress obtained after stopping laser irradiation in the LSC or vision correction surgery allows the user to forecast regarding the stability of the results. By the detection of substantial heterogeneities of the residual stress (as can be determined with the use of an optoacoustic technique or a multi-sectional pneumatic system) a repeated laser treatment is recommended to lead to stress relaxation and more stable results of laser reshaping.

Examples of Combinations of Measurements

As described above in the Overview, System Configuration, and Method of Operation sections, monitoring any single characteristic of a tissue treatment site does not guarantee safety and efficacy of laser reshaping and regeneration procedures. It is only through a combination of measurement techniques that safety and efficacy can be ensured. In this section, specific non-limiting examples are provided to illustrate these points.

Laser Regeneration Treatments

In laser regeneration treatments, measurement of a light scattering signal shows the beginning and development of the micro-cavitations process followed by the pore formation process, which is necessary for cell nutrition and tissue regeneration. Micro-bubbles can form as a result of either processes; however, it is unclear from light scattering measurements alone which micro-bubbles correspond to which process. Thus, additional measurements are needed to distinguish between the two types of micro-bubbles. Temperature measurements show the temperature of the bubbles and allow the separation of the conditions for the micro-cavitations process (i.e., occurring at relative low temperatures) from the vaporization process (i.e., requiring higher temperatures and resulting in tissue damage). Temperature measurements during laser treatment allow the decrease of laser power or the stoppage of the laser treatment when the limit of the permissible temperature is achieved. Whether to decrease the laser power or stop irradiation depends on the degree of the pore system maturity, which can be established using electrical measurements. It is only through the combination of the above measurement that the practitioner can obtain a safe and positive result of treatment.

Laser Reshaping Treatments

In laser reshaping treatments, the efficacy of the technology is governed by the occurrence of stress relaxation in the tissue, while the safety of the technology is controlled by the absence of tissue denaturizing and damage. By using speckle interferometry, the user can monitor water transport through the tissue; and when used in combination with temperature measurements, the user can safely approach and avoid the threshold of tissue denaturizing. Water transport under external compression of nasal septum cartilage can be important for decreasing laser radiation absorption by mucosa, which in turn reduces tissue surface temperature and prevents damage of the mucosa. Temperature measurement (e.g., as made using a thermocouple sensor or radiometer sensor) can be used to determine tissue temperature, which in turn allows the user to achieve efficacious temperatures for tissue reshaping and enabling a decrease in laser power before tissue damage occurs. Optoacoustic measurement allows the user to monitor changes in the treated tissue's mechanical properties in the course of laser irradiation.

For optoacoustic measurements, it can be favorable to use a diagnostic laser having sharply defined radiation pulses. In various aspects, the diagnostic laser pulses have considerably lower energy by comparison to the laser pulses used for laser medical treatment. It is thought that high-powered lasers, such as those used for many laser medical treatments, can damage cells and the intercellular matrix if sharply defined laser pulses are used.

In order for tissue reshaping to be effective, there must be a minimization of any non-uniform residual stresses (i.e., stress relaxation). Residual stress distribution can be measured by optoacoustic measurement. By using optoacoustic measurement, it is more likely that the stress relaxation process will occur, which contributes favorably to tissue reshaping. The long-term stability of the new tissue shape obtained by laser reshaping depends on the residual stress distribution in the tissue. In various aspects of the present disclosure, laser reshaping is performed by application of laser radiation until the non-uniformity of the residual stress is below a threshold level, thereby increasing the stability of the post-treatment tissue. By contrast, if the treatment is terminated while the residual stress is above the threshold level, the post-treatment tissue can undergo further unintended changes in shape following treatment. The present disclosure provides a safe and efficacious method for performing tissue reshaping through the use of a combination of temperature and optoacoustic measurement. No single measurement that is currently known is capable of achieving these levels of efficacy and safety.

Laser Regeneration of Joint Cartilage

For laser regeneration of joint cartilage, a spectra of reflected (i.e., back scattered) light is measured at various points across the cartilage surface. These measurements allow the user to characterize the spatial distribution of absorption and scattering coefficients across the tissue, which correlates with tissue characteristics and allows the user to make preliminary determinations regarding the laser settings (e.g., laser power and pulse duration). Cartilage having large pores produces an identifiable spectrum that can be measured by light scattering measurements. When the reflected light spectrum indicates the presence of large pores in the cartilage, a pre-defined action can be taken. The predefined action can be, for example, the delivery of a drug of interest to the cartilage matrix, adjusting laser power, or switching the laser off. Any suitable drug can be delivered, for example, chondro protectors such as glucosaminoglycanes, hyaluronic acid, or a combination thereof.

Speckle interferometry can be used to determine the rate of introduction of the drug of interest into the cartilage matrix. In certain aspects, speckle interferometry is used to determine whether laser power should be adjusted. For example, in certain aspects, laser power can be increased from "medium" to "high" to affect the porosity of the cartilaginous tissue, thereby increasing the rate at which the drug of interest is introduced into the cartilage matrix. In further aspects, speckle interferometry can be used to show the variations in cartilage optical properties. Based on those measurements, the laser settings can be modified (e.g., by decreasing laser power or increasing pulse duration). In the event a more degenerated area is detected, it can be useful to decrease pulse duration from 0.5 to 0.2 seconds. By obtaining temperature measurements in the course of laser treatment, the user can control the tissue temperature and approach and avoid the threshold temperature above which tissue damage occurs.

The present disclosure provides a safe and efficacious method for performing laser regeneration of joint cartilage through the use of a combination of light scattering measurements, speckle interferometry, and temperature measurements. No single measurement that is currently known is capable of achieving these levels of efficacy and safety.

Laser Reshaping of Throat Cartilage

For laser reshaping of throat cartilage, photoacoustic tomography measurements allow for the visualization of the throat cartilage topography that is to be reshaped. Photoacoustic tomography can also be used to assist the user in identifying and selecting the preliminary laser settings (e.g., laser wavelength, power and exposure time). In the course of laser treatment, photoacoustic tomography provides information regarding alterations in cartilage thickness and provides an indication of whether and when laser wavelength or exposure time should be adjusted to account for thicker cartilage. In certain aspects, the laser generation module 122 provides a treatment pattern. For laser reshaping of cartilage, the treatment pattern can be characterized by two spacing parameters, the first parameter being the separation between the laser spots in a line (e.g., from 1 to 2 mm); and the second parameter being the separation between the treatment lines (e.g., from 2 to 4 mm). These spacing parameters can be adjusted to account for cartilage topography and heterogeneity of stress distribution in the laser-treated zone. For example, when the sensor data shows that heterogeneity of residual stress is high (i.e., the spacing between zones with differing stresses is of approximately 4 mm), the separation between the treatment lines can be decreased from 4 mm to 2 mm. In further aspects, when there is a localized area with high relative stress, the spacing between laser spots can be decreased (from 2 to 1 mm). By obtaining temperature measurements in the course of laser treatment, the user can control the tissue temperature and approach and avoid the threshold temperature above which tissue damage occurs.

By obtaining photoacoustic tomography measurements in the course of laser reshaping of throat cartilage, the user can be prompted to adjust the spacing between laser spots (e.g., decrease from 2 mm to 1 mm) in the area of maximum tissue stress in cartilage. Moreover, by using photoacoustic tomography, the user can be prompted to discontinue laser irradiation once non-homogeneity of the residual stress is reduced below a threshold level, thereby indicating that the tissue has been stabilized.

In some aspects, the laser generation module 122 provides a treatment pattern, wherein the treatment pattern is selected in order to account for tissue non-homogeneity and to alternate between treated and untreated areas of the tissue. In this aspect, the spacing can be, for example, from 0.5 to 5 mm. For laser reshaping of cartilage, the treatment pattern can be characterized by two spacing parameters, the first parameter being the separation between the laser spots in a line (e.g., from 1 to 2 mm); and the second parameter being the separation between the treatment lines (e.g., from 2 to 4 mm). These spacing parameters can be adjusted to account for cartilage topography and heterogeneity of stress distribution in the laser-treated zone. For example, when the sensor data shows that heterogeneity of residual stress is high (i.e., the spacing between zones with differing stresses is of approximately 4 mm), the separation between the treatment lines can be decreased from 4 mm to 2 mm. In further aspects, when there is a localized area with high relative stress, the spacing between laser spots can be decreased (from 2 to 1 mm). For laser regeneration of joint cartilage, the separation between the laser spots is typically 1.5 mm. This spacing can be adjusted for thinner cartilage areas or for small damaged or degenerated zones of cartilage to be treated, for example, the spacing between laser spots can be decreased from 1.5 mm to 1.0 mm. For large, relatively homogeneous zones, the spacing between laser spots can be increased, for example, from 1.5 mm to 2.0 mm. The present disclosure provides a safe and efficacious method for performing laser reshaping of throat cartilage through the use of a combination of photoacoustic tomography and temperature measurements. No single measurement that is currently known is capable of achieving these levels of efficacy and safety.

Configuration of Tool

FIGS. 3-11 illustrate aspects of a tool subsystem 110 for use with the laser system 100 in accordance with various aspects of the present disclosure. FIG. 3A-C illustrates a tool for use with the laser system 100 in accordance with an aspect of the present disclosure. The tool according to FIG. 3A-C serves as a diagnostic and control system and can include a tissue contactor 312 with a radiometric temperature sensor and an IR fiber delivery module 305 for the administration of thermal radiation at the tissue contactor 312 of the tool 300.

As shown in FIG. 3, the tool 300 can include a body 301, cylinder 302, prism 303, optical fiber or fiber bundle 304 and 305, radiometric detector 306, digital preamplifier 307, electrical connector 308, optical connector 309, prism house 310, and a fiber support 311. In various aspects, the tool 300 is modular. The tool 300 can comprise a fiber optic module 304 for delivery of the working and diagnostic laser beams to the tissue treatment area, fiber optic module 305 for delivery of the diagnostic beam from the tissue treatment area to the sensor, sensor module (e.g., a radiometric detector 306), optical adapter (e.g., a prism 303), which performs mixing and splitting of the working and diagnostic beams, and a contactor module 312 that mechanically interfaces with the tissue. In some aspects, the fiber optic module 304 can also be used for delivery of the diagnostic laser beams to the tissue treatment area, as well as for collecting and delivery of diagnostic light to the sensor module. In this case, an optical adapter that facilitates mixing and splitting of the working and diagnostic beams can be positioned at the inlet of the fiber optic module 304.

The body of the tool 301 can be any suitable configuration for practicing the present methods. For instance, the body 301 can be configured such that it is capable of being held in a single hand for handheld use. Alternatively, the system can be configured for remote operation using a remote link (wired or wireless).

The cylinder 302 can have a hollow configuration in order to accommodate multiple sensor components such as, for example, wires and fiber optics. The prism 303 can be housed in a prism house 310. In some aspects, a prism 303 can be used as an optical adapter between the working and diagnostic beams. The prism 303 is applied for deflecting and aiming of the working laser beam and diagnostic light to the same target area of the tissue to be treated. To provide such function, the front surface of the prism comprises two mutually inclined facets refracting suitable beams to different angles, but centering them on the same point of the tissue surface. Given the tight configuration of the cylinder 302 and contactor module 312, this mechanism can be used for alignment of the optical axes of both sets of optical fibers 304 and 305 to the same point.

The tool 300 can include one or a plurality of fiber optics for delivery of laser beams for diagnosis and/or therapeutic purposes. A fiber optic module 304 can be used for illumination of a tissue by a diagnostic (i.e., probing) beam and/or therapeutic (i.e., working) laser beam. Both beams can be transmitted by fiber optics, and each can be integrated into fiber optical bundles 304 and 305, respectively. In some aspects, a quartz optical fiber 304 can be used for the collection of light for optical measurements (e.g., speckle, luminescence, and scattering measurements), which enables dynamic control using a feedback mechanism of the tool 300 by a practitioner and/or as provided by a predefined rule. The tool 300 can be used to measure radiation of different spectral ranges simultaneously, for example, near infrared for the working beam of Er:Glass (wavelengths of 1.54-1.56 microns) laser and middle/far infrared for diagnostic light for temperature measurement by IR radiometer (wavelengths of 3-12 microns). Therefore the materials of the optical elements 304 and 305 should be selected such that they can transmit light of the desired wavelength. The particular configuration of the tool 300 as depicted in FIG. 3 can be used for the thermal treatment of biological tissues by laser radiation with radiometric control of the temperature in the treated area. In this aspect, the core of the fiber optic 304 preferably comprises quartz, the prism 303 preferably comprises a nonhygroscopic salt such as $BaF_2$, and the core of the fiber optic 305 preferably comprises silver halides, such as for example AgI/AgBr polycrystals. Any suitable temperature sensor (e.g., a radiometric detector 306 or spectroscopic detector) can be used according to the present disclosure. In some aspects, a digital preamplifier 307 can be employed in order to magnify the signals obtained via the diagnostic system of the tool 300. For instance, digital signals can be amplified in order to increase the signal-to-noise ratio of measurements relating to tissue characteristics. In some aspects, an electrical connector 308 can be used for the transfer of electrical signals obtained from the sensors of the tool 300 to a sensor processing module. The electrical signals arising from the sensors can ultimately be analyzed by a computer and used to provide feedback for modifying treatment conditions. In some aspects, an optical connector 309 can be used to deliver and/or receive light to and from the tool 300. In some aspects, diagnostic information can be received from the tool 300 following delivery of diagnostic laser irradiation. In various aspects, therapeutic light is delivered to the tool 300 in the form of a laser beam. In some aspects, a fiber support 311 can be used for supporting the tips of fibers 304 and 305 at the appropriate positions with respect to each other and prism 303. The fiber support 311 can in certain aspects comprise a short-length rod fitted to the internal diameter of the cylinder 302 with two holes into which the fibers 304 and 305 can be suitably centered.

The signal detected by the sensors can then be analyzed by a computer. The system can non-invasively measure the properties of the tissue and process the measurement values using a computer model to enable selection of a tissue treatment site, to identify threshold conditions that trigger a change in treatment conditions, and to initiate changes in treatment conditions in response to changes in the properties of the treated tissue. Thus, the measurements obtained can be used for continuous feedback control of the therapeutic laser in order to deliver effective and non-destructive irradiation to the tissue. In accordance with an aspect of the present disclosure, software algorithms can be employed that are designated for various types of procedures and tool modules for performing the procedures. The measurement signals are analyzed by the computer and give rise to an output signal, which in turn produces particular output conditions by the tool. In this manner, a single instrument can be used to perform a number of measurements and to produce a range of outputs. The system can function under the control of specified algorithms and/or by control of a practitioner. The system is capable of responding in real time to tissue condition measurements in order to customize treatment for a particular procedure, subject, and tissue. Any number of suitable tissue measurements can be used in combination in order to give rise to customized, efficient, and safe treatment of tissues.

Figure 4:
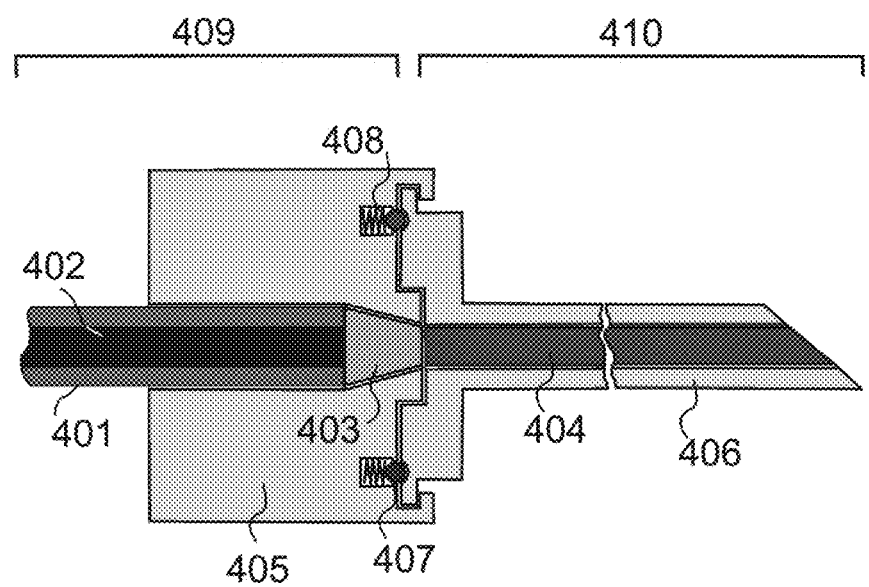
FIG. 4 illustrates a locking mechanism of the tool, in accordance with an aspect.

FIG. 4 illustrates a locking mechanism 400 of the tool, in accordance with an aspect of the present disclosure. As shown in FIG. 4, the locking mechanism 400 can include a diagnostic optical fiber 401, working radiation optical fiber 402, optical adapter 403, fiber-optic irradiator 404, mechanical adapter 405, body (needle) 406, ball 407, and spring 408. The tool 400 can be used for a variety of therapies, including, without limitation, the treatment of deviated and damaged cartilaginous tissues. The tool 400 can include one or a plurality of fiber optic bundles for delivery of laser beams for tissue condition diagnosis and/or therapeutic purposes. Fiber optic bundles can be used for illumination of a tissue by a diagnostic laser beam and/or a therapeutic (i.e., working radiation) laser beam. Both laser beams can be integrated into fiber optical bundles 401 and 402, respectively. In some aspects, a diagnostic optical fiber 401 can be used for the collection of light for optical measurements (e.g., speckle and scattering measurements), which enables dynamic control or the tool 400 by a practitioner and/or as provided by a predefined rule.

In various aspects, an optical adapter 403 can be used for interfacing the diagnostic optical fiber 401 and working radiation optical fiber 402 with the fiber optic irradiator 404, which is housed within the body (needle) 406. The fiber optic irradiator 404 delivers therapeutic and/or diagnostic radiation pulses to the tissue and/or receives radiation from the tissue, such as for diagnostic measurements (e.g., speckle and scattering measurements). In some aspects, the optical adapter 403 can also include optical connectors and one or more lenses for facilitating the delivery of radiation to and/or receipt of radiation from the tissue.

In certain aspects, the locking mechanism 400 can comprise two interfacing subunits 409 and 410, the first subunit 409 comprising the working optical fiber 402, the diagnostic optical fiber 401, the optical adaptor 403, and one or more springs 408; and the second subunit 410 comprising a fiber optic irradiator 404 embedded in the body 406 and one or more balls 407. The springs 408 can be positioned in slots in the first subunit 409, which project the balls 407 out of a slot. The tool can be configured such that the slotted end is narrowed in order to prevent the balls from falling outside of the slot. In some aspects, the second subunit 410 can comprise notches into which the projecting portion of the balls 407 can interface by rotating subunit 409 relatively to unit 410 around a common axis. The one or more slots in the first subunit 409 are positioned such that they align with the one or more notches in the second subunit 410 when the first subunit 409 and second subunit 410 of the locking mechanism are positioned together. The two subunits 409 and 410 can then be latched into place under tension using a mechanical adapter 405, which causes the subunits 409 and 410 to become locked securely into an aligned position. Thus, the locking mechanism 400 can be used to fix the relative position of the two sliding cylinders (i.e., the first and second subunits) with respect to both longitudinal and rotational motions.

Figure 5:
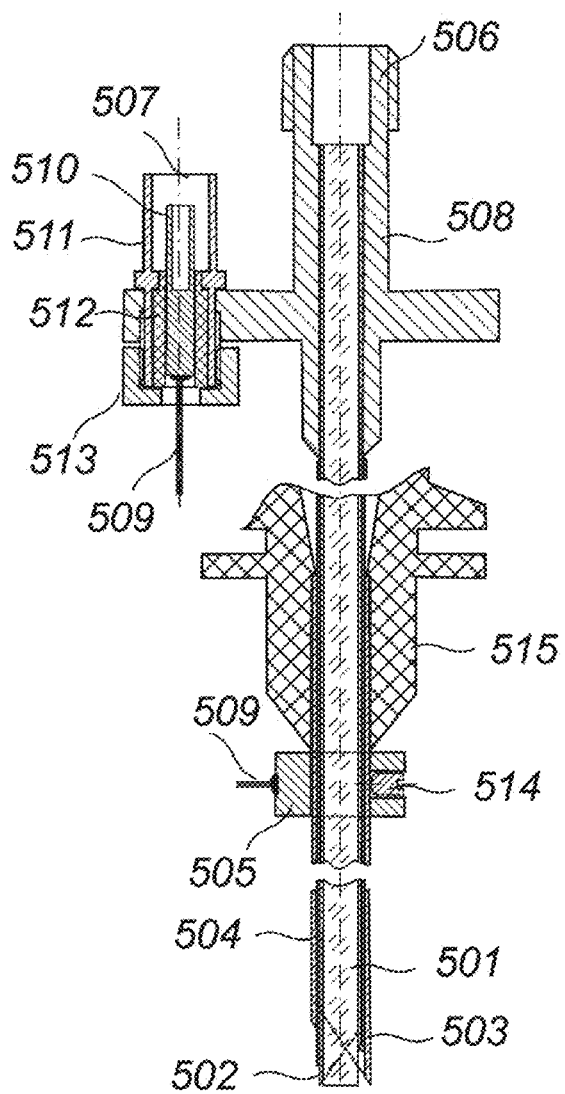
FIG. 5 illustrates another example of a tool for use with the laser system in accordance with an aspect of the present disclosure.

FIG. 5 illustrates another example of a tool 500 for use with the laser system, in accordance with an aspect of the present disclosure. As shown in FIG. 5, the tool 500 can include an optical fiber 501, resistance sensor having a chamfered end 502, chamfered metal (i.e., conductive) body 503, conductive fiber shell with an insulating cover 504, current collector 505, optical connector 506, and electrical connector 507. In some aspects, the instrument 500 can be used for the measurement of electrical impedance of tissue in the course of laser medical treatment of cartilaginous tissues.

In certain aspects, the instrument 500 can have two coaxial conductive cylinders with an optical fiber 501 inside and a resistance sensor on its distal end 502. An optical connector 506 and electrical connector 507 are positioned on the proximal end of the instrument body 508 and enable interfacing of the optical and electrical components, respectively. The proximal end of instrument body 508 can be made from conductive material and can serve as a conduit of electrical current from the resistance sensor 502 to the electrical connector 507. The electrical connector can comprise a conductive case 511, pin 510, resistive bushing 512, and screw nut 513. The current collector 505 can be used for measuring the electrical properties of the tissue in the course of medical treatment as recorded at the resistance sensor 502. The measurement can be taken by transporting the electrical current via the champhered conductive body 503 and wire 509 to the pin 510 of the contactor 507. The current collector 505 can be attached to the champhered conductive body 503 before medical treatment using a screw 514. Those measurements can then be used to provide feedback regarding laser output conditions during the laser treatment of tissue.

The optical fiber 501, chamfered end of the resistance sensor 502, chamfered body 502, and conductive fiber shell with insulating cover 504 are configured together in the instrument 500 to form a laser emitter with a resistance sensor 502. The resistance sensor 502 is used to characterize tissue conditions in the course of laser treatment and to control the laser treatment regime. In certain aspects, the resistance sensor 502 can be positioned along the instrument body and can be controlled with a positioning sensor which fixes the insertion depth of the laser emitter into the tissue. In some aspects, the instrument body 503 also includes a fiber tuning sensor to ensure non-traumatic insertion of the fiber into the tissue to be irradiated.

The electrical properties of the treatment tissue depend on its structure. The presence of pores in the tissue will increase the tissue's impedance. Deaggregation of the proteoglycan component of the cartilage matrix will increase the mobility of charged groups thereby increasing the electrical current through the tissue. Variation of the insertion depth allows to the user to characterize the spatial distribution of the structural defects, in particular the pores and destroyed zones of cartilage matrix.

The instrument body 503 can be a serial biopsy needle of appropriate size with a holder 515, a part of which is depicted in FIG. 5. As demonstrated in FIG. 6, the serial biopsy needle can be compatible with the locking mechanism 600. In this aspect, a fiber optic can pass along the longitudinal axis of the tool, thereby enabling the longitudinal motion and axial rotation relative to the instrument body and further enables the fiber optic to be fixed in place within the tool. As shown in FIG. 5, the chamfered end of the resistance sensor 502 and a chamfered body 503 are oriented such that both chamfers are aligned in the same plane in order to ensure that insertion is minimally traumatic. After insertion of the instrument into the tissue, the optical fiber 501 can be turned 180 degrees to obtain a dovetail configuration. In some aspects, a force transducer can be rigidly connected with an optical fiber 501 to control the insertion process of the laser emitter into the tissue.

In some aspects, the proximal end of the locking mechanisms and fiber optic shell can comprise special markings indicating a proper angular and longitudinal position of the fiber optic 501 relatively to the instrument body.

In certain aspects, the instrument 500 can also include a hollow body that can accommodate various components (e.g., fiber optic bundles or sensor wiring), sensors (e.g., electrical resistance sensors), radiation delivery units (e.g., an optical fiber or bundles of optical fibers), radiation formation units, and a diagnostic units for the auxiliary diagnosis (e.g., optical or mechanical) of affects on the tissue.

In certain aspects, the mechanical characteristics of the irradiated tissue can be controlled by applying mechanical oscillations to the instrument body 503 by integration of a mechanical oscillator into the device. Any suitable amplitude and frequency can be used. Application of mechanical oscillations to tissue such as cartilage leads to the movement of water through the tissue. The water moves from the stressed areas of the tissue to the expanded areas of the tissue. The process of stress relaxation in cartilage requires the input of energy. Therefore, measuring the internal friction during mechanical oscillations enables the user to monitor the processes occurring in the course of heating and during laser treatment. For example, a reduction of the mechanical oscillation frequency (or energy) can suggest that the process of stress relaxation in cartilage has been completed. Significant decreases in the oscillation energy can suggest that denaturation or tissue damage is occurring. A signal of this type, together with other signals, for example dramatic temperature increases, can suggest that treatment should be discontinued. The mechanical oscillator transducer can be positioned on the proximal end of optical fiber 507, which can serve as an acoustic line.

Figure 6:
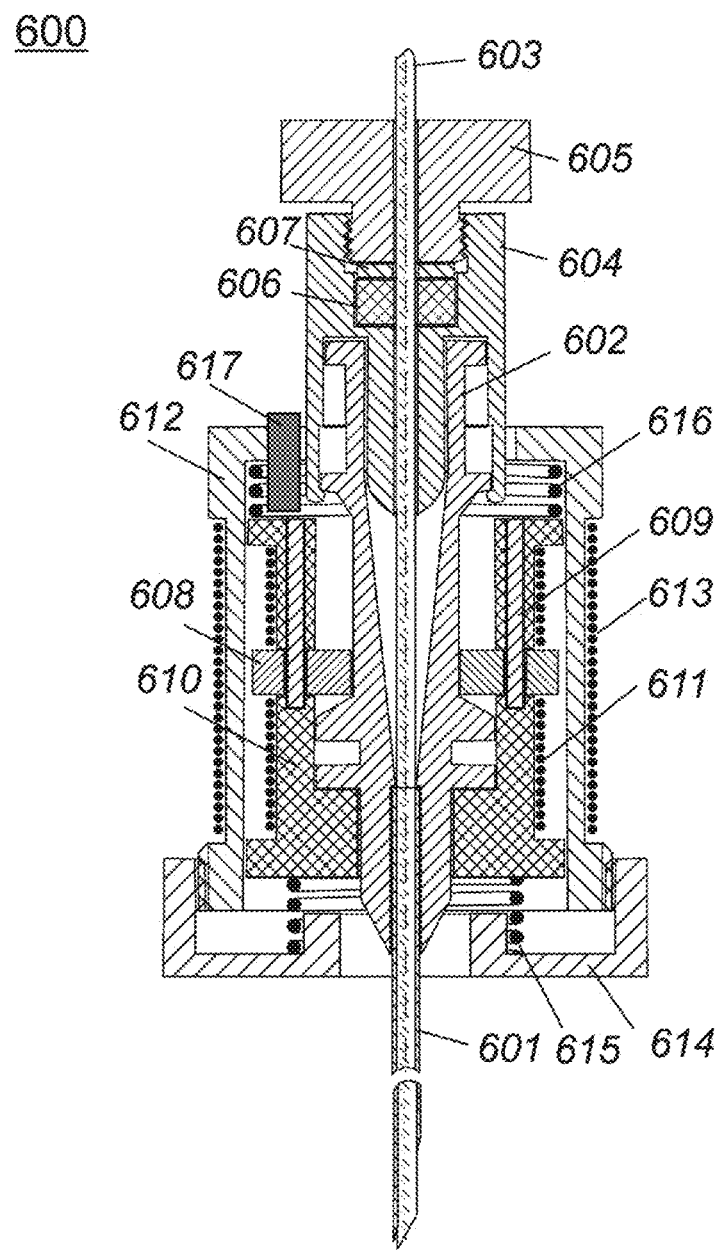
FIG. 6 illustrates a hollow body of the tool assembled with a locking mechanism in accordance with an aspect of the present disclosure.

FIG. 6 illustrates a vibration mechanism 600 of the tool, in accordance with an aspect of the present disclosure. As shown in FIG. 6, the vibration mechanism can be assembled in conjunction with a hollow body and locking mechanism. In certain aspects, the vibration mechanism comprises a spool 610 and frame 612. In some aspects, the spool 610 comprises a built-in clipping mount with axle 609, presser feet 608, and core coil 611. In certain aspects, the frame 612 comprises an induction coil 613, lower spring 615, upper spring 616, and closure head 614. The hollow body can be connected to the spool 610 using the clipping mount. The lower spring 615 and upper spring 616 facilitate longitudinal motion of the hollow body along with the locking mechanism and spool assembly 610 relative to the frame 612. In certain aspects, the vibration mechanism can be fixed to a holder of the hollow body. In other aspects, the vibration mechanism can be detached from the holder of the hollow body. In certain aspects, a mandrel can be positioned within the needle for added stability during needle insertion. The mandrel can then be replaced with an optical fiber following needle insertion and during the medical treatment process.

The core coil 611 and induction coil 613 can be supplied with continuous or alternating electrical current from a power supply through an electrical connector (not shown). The action of the vibration mechanism on a tissue alters the tissue's physical and chemical properties. In certain aspects, the effect of the vibration mechanism on the tissue can be determined by the amplitudes of current in the induction coil 613 and core coils 611. The magnitude of displacement of the spool 610 (and thus the connected hollow body) relative to the frame 612 can be detected by a proximity sensor 617 which can be mounted on the frame 612, thus enabling control of the degree of displacement. The proximity sensor can be responsive to any suitable stimuli, such as for example, capacitive or photoelectric stimuli. The proximity sensor can be, for example, an eddy current probe.

Vibration of the vibration mechanism is achieved in certain aspects by producing an alternating force between two coils or between a coil and a magnet as a result of applying an electrical current through the coil(s). Thus, one of the two coils (i.e., one of the core coil 611 or induction coil 613) can optionally be replaced by a permanent magnet of suitable shape.

Figure 7A:
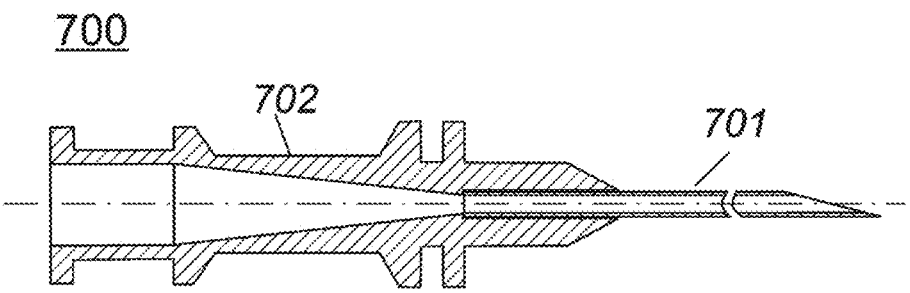
FIG. 7A-C illustrate a hollow body, locking mechanism, and clipping mount of the tool according to one aspect of the present disclosure.

FIG. 7A illustrates a hollow body member 700, in accordance with an aspect of the present disclosure. In some aspects, the hollow body member 700 can be similar to a serial biopsy needle. In other aspects, the hollow body member 700 comprises a metallic entry needle 701 positioned within a needle housing 702. In certain aspects, the needle housing 702 can comprise plastic or any other suitable material. The needle housing 702 can optionally comprise raised features such as for example, concentric ribs, for improved gripping, ergonomic handling, and mechanical safety.

Figure 7B:
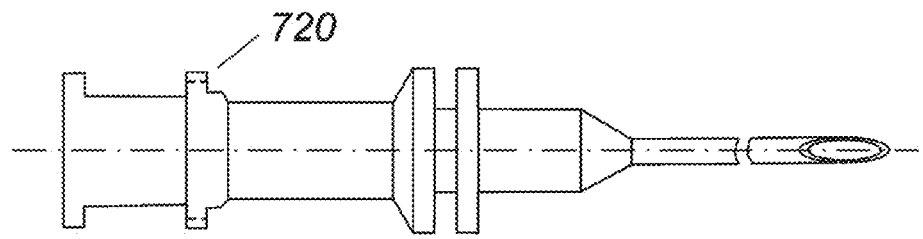

FIG. 7B illustrates recesses 720 within the needle housing 702 that can be used in certain aspects of the present disclosure for fixation and immobilization of the mandrel during entry of the needle into the tissue to be treated. The recesses 720 can also be used for fixation of the locking mechanism. In certain aspects, the recesses can be positioned such that they are concentric with the needle housing 702.

Figure 7C:
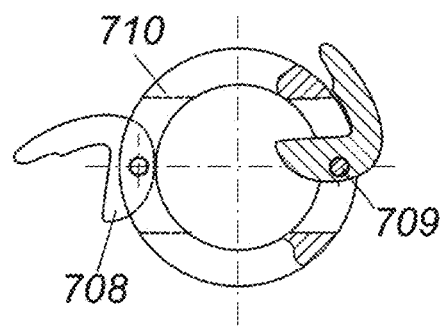

FIG. 7C illustrates a clipping mount 730 which can be used in certain aspects of the present invention for connection of the hollow body with the vibration mechanism. In some aspects, the clipping mount 730 comprises presser feet 708 which can be positioned concentrically with the axles 709. Slots within the frame of the clipping mount 730 facilitate the rotation of the presser feet. The clipping mount 730 can advantageously be designed to ergonomically fit within the human hand. The hollow body can be inserted into the clipping mount 730 when the presser feet 708 are open as shown on the left side of FIG. 7C. The hollow body can be fixed and immobilized within the clipping mount 730 by closing the presser feet 708 as shown on the right side of FIG. 7C.

Figure 8:
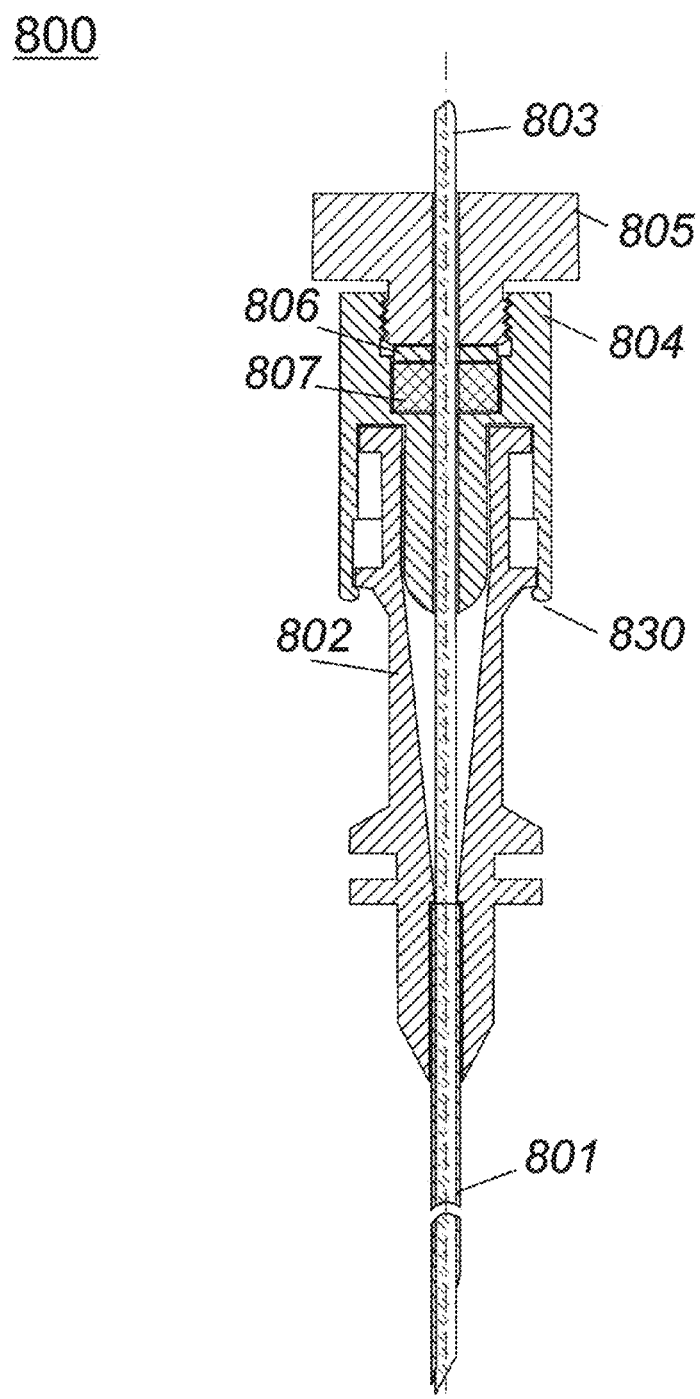
FIG. 8 illustrates a hollow body of the tool fixed in place by a locking mechanism according to one aspect of the present disclosure.

FIG. 8 illustrates one aspect of the present disclosure including a hollow body 800 comprising an interior locking mechanism. In this aspect, an optical fiber 803 can be positioned within the hollow body 800. According to this aspect, the locking mechanism comprises a mechanical adapter 804, fixing bolt 805, washer 806, and packing gland 807. The mechanical adapter 804 can be inserted partially into the needle housing 802 in order to stabilize the position of the mechanical adaptor 804 within the hollow body 800 and to facilitate its connection to the hollow body 800. In certain aspects, the mechanical adaptor 804 is connected to the hollow body 800 by a spring fastener 830. In this aspect, the spring fastener 830 can be positioned within the recesses 720 of the needle housing 802. In certain aspects, the mechanical adapter 804 and its holder can be disconnected with relative ease, for example, they can be removed by hand. The mechanical adaptor 804 can comprise internal threading. In some aspects, the fixing bolt 805 can be threaded into the mechanical adaptor 804. In various aspects, each of the elements of the locking mechanism comprises through-holes through which an optical fiber 803 can be passed. In some aspects, the device comprises a compressible packing gland 807 that is positioned adjacent to a washer 806 and surrounding an optical fiber 803. As the fixing bolt 805 is threaded into the hollow body 800, it presses on the washer 806 and packing gland 807. As the packing gland 807 is pressurized, it expands radially, thereby fixing and immobilizing the optical fiber 803 within the hollow body 800. The optical fiber 803 can be released by unscrewing the fixing bolt 805 from the hollow body 800 and thereby releasing the pressure on the washer 806 and packing gland 807.

Figure 9A:
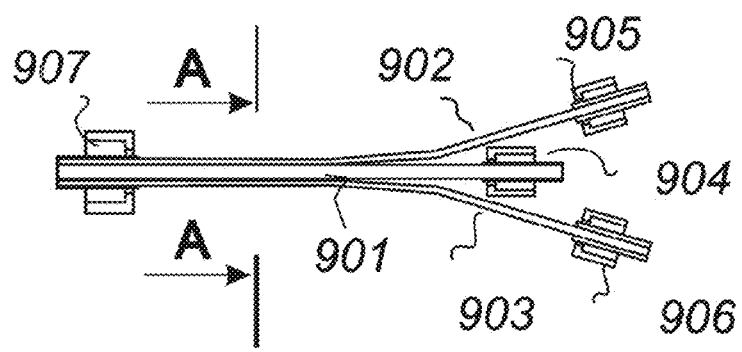
FIG. 9A-B illustrate an example of an optical adapter of the tool in accordance with an aspect of the present disclosure.
Figure 9B:
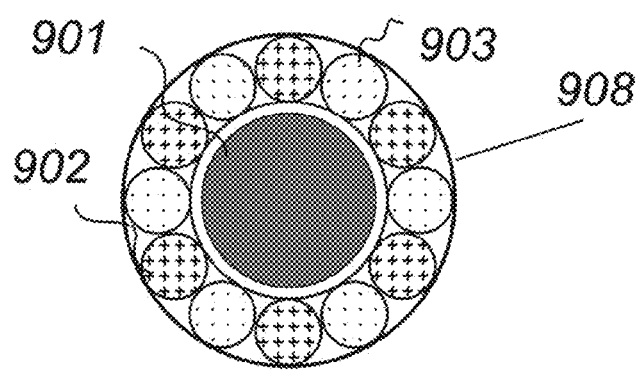

FIG. 9A illustrates an optical adapter 900 according to one aspect of the invention. The optical adapter 900 can be used for the mixing or splitting of a working laser beam and diagnostic radiation within a distal optical fiber (not shown). FIG. 9B depicts a cross-sectional view of the optical adapter 900. In some aspects, the optical adapter 900 can comprise a central optical fiber 901 or optical fiber bundle 901 and a number of surrounding peripheral optical fibers that can in some aspects be bundled into two separate optical fiber bundles 902 and 903. These optical fibers can in certain aspects be collectively bundled into a common optical bundle 908 that can be embedded into the optical connector 907. The central optical fiber 901 and optical fiber bundles 902 and 903 can be embedded within the optical connectors 904, 905, and 906, respectively, at their proximal ends. In some aspects, the distal optical fiber (not shown) can be connected with the optical adapter 900 by the optical connector 907. The working laser beam can be delivered to the optical adapter 900 through the optical connector 904 and then to the distal optical fiber through the optical connector 907. Similarly, a diagnostic light can be delivered to the distal optical fiber through the optical connectors 905 and 907. In further aspects, the returning diagnostic radiation can be transmitted through the optical connectors 906 and 907 to the optical sensor.

Figure 10A:
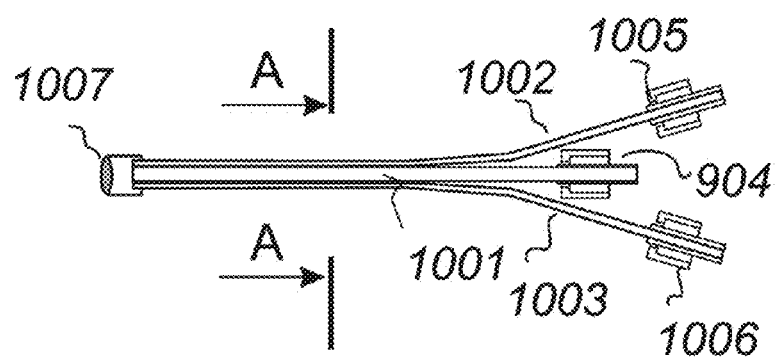
FIG. 10A-B illustrate a second example of an optical adapter of the tool in accordance with an aspect of the present disclosure.
Figure 10B:
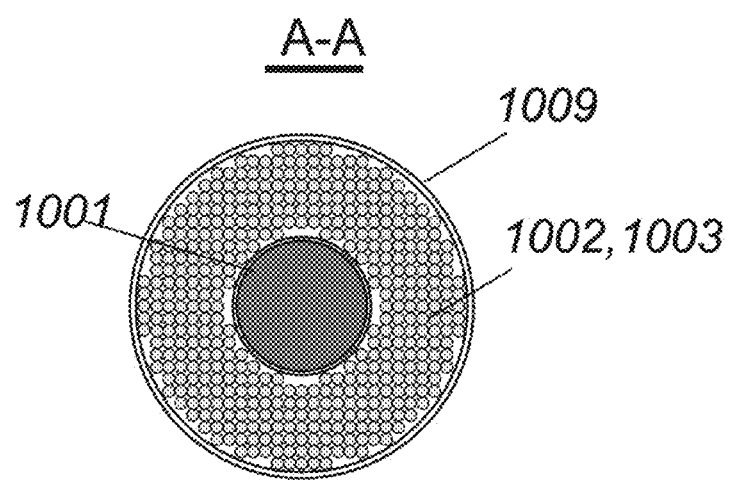

FIG. 10A illustrates a distal fiber bundle 1000 according to one aspect of the present disclosure. The distal fiber bundle 1000 can be used with any suitable diagnostic method, for example, the distal fiber bundle 1000 can be used in conjunction with speckle dynamic diagnosis of thermal modification of a biological tissue. FIG. 10B depicts a cross-sectional view of the distal fiber bundle 1000. The distal fiber bundle 1000 can comprise a central optical fiber 1001 or an optical fiber bundle 1001 and a number of surrounding peripheral optical fibers which bundled in two separate optical fiber bundles 1002 and 1003. Together, these optical fibers can be bundled into a common optical bundle 1009. The working laser beam can be delivered to the tissue area to be treated through an optical connector 1004 and central optical fiber 1001. The treated tissue area can be illuminated by a diagnostic coherent light using the central optical fiber 1001, or through a bundle 1002. In some aspects, speckle dynamic measurement can be performed by a CCD camera or photodiode array that can be positioned at the proximal end of the fiber bundle 1003. The distal end of this bundle can be polished and can further comprise an imaging lens 1007. In certain aspects, the diameters of the peripheral fibers 1002 or 1003 are sufficiently small such that they are capable of providing measurements of the intensity of a single speckle that can be created on the face plane of the bundle 1009 by the lens 1007. In certain aspects, the device as depicted in FIGS. 10A and 10B comprises a central optical fiber 1001 that transmits the working laser beam and a set of peripherally located fibers bundled at the proximal ends of the distal fiber bundle 1000. In this configuration, the tool can be used to illuminate the tissue with a plurality of diagnostic beams and to simultaneously collect the returning radiation for measurement and analysis through the respective optical bundles.

Figure 11:
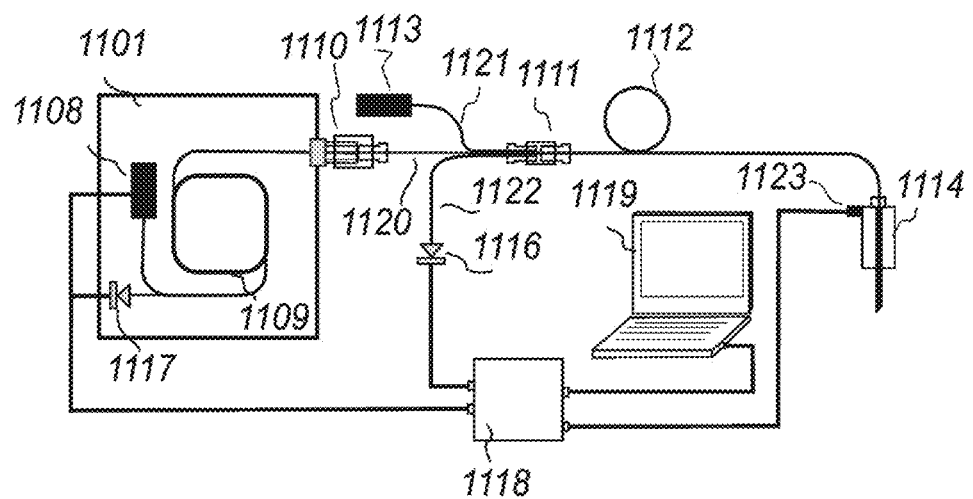
FIG. 11 illustrates an example of the laser system in accordance with an aspect of the present disclosure.

FIG. 11 depicts the components of the tool 1100 for the laser treatment of biological tissues according to one aspect of the present disclosure. As shown in FIG. 11, the tool 1100 can comprise a fiber laser system 1101, which comprises a laser source 1108, laser power controller 1117, and fiber delivery system 1109. The tool 1100 can further comprise an optical adapter comprising a central optical fiber 1120, two peripheral optical fibers 1121 and 1122, and a distal optical fiber 1112. According to this aspect, the tool further comprises a vibration mechanism 1114 with an eddy probe 1123 for the displacement control. The tool 1100 further comprises a source of diagnostic light 1113, an optical sensor 1116, optical connectors 1110 and 1111, a data acquisition and processing module 1118, and a computer 1119.

In certain aspects, the tool can be configured such that it is capable of releasing drugs into the treatment tissue. The tool can comprise a tubule to deliver a drug solution or a hole to introduce a tubule for this purpose. The tissue properties can be modified and monitored such that release of the drug from the instrument occurs under tissue conditions wherein drug delivery to the tissue of interest is optimized. The predefined action can be, for example, the delivery of a drug of interest to the cartilage matrix, adjusting laser power, or switching the laser off. Any suitable drug can be delivered, for example, chondro protectors such as glucosaminoglycanes, hyaluronic acid, or a combination thereof.

Although the detailed description contains many specifics, these should not be construed as limiting the scope of the invention but merely as illustrating different examples and aspects of the invention. It should be appreciated that the scope of the invention includes other aspects not discussed in detail above. Various other modifications, changes and variations which will be apparent to those skilled in the art can be made in the arrangement, operation and details of the method and apparatus of the present invention disclosed herein without departing from the spirit and scope of the invention.

What is claimed is:

1. A device for laser treatment of cartilaginous tissues, the device comprising:
   a handheld tool comprising:
      a cylinder having a lumen, a proximal end, and a distal end, the cylinder having a longitudinal axis along a length of the cylinder from the proximal end to the distal end;
      a working optical fiber passing through the lumen of the cylinder and configured to transmit through the lumen a first beam of laser light having properties comprising a wavelength, power, pattern, and pulse profile, wherein the first beam of laser light is configured to produce a working radiation that provides a non-destructive irreversible modification of a cartilaginous tissue;
      a diagnostic optical fiber passing through the lumen of the cylinder and configured to transmit through the lumen a second beam of laser light having properties comprising a wavelength, power, pattern, and pulse profile, the second beam of laser light configured to produce a diagnostic radiation or to receive diagnostic light from the cartilaginous tissue;
      a fiber-optic irradiator housed within the cylinder at the distal end and configured to deliver one or both of the working radiation and the diagnostic radiation to the cartilaginous tissue;
      an optical adapter housed within the cylinder, the optical adapter interfacing the diagnostic optical fiber and the working optical fiber with the fiber-optic irradiator for delivery of the first or second beams of laser light;
      a locking mechanism of the cylinder, the locking mechanism comprising a first subunit and a second subunit, the first subunit comprising at least one spring positioned in a slot, and the second subunit comprising at least one ball, the ball configured to compress the spring into the slot in a direction parallel to the longitudinal axis of the cylinder, wherein the first and second subunits are structurally configured to securely engage with each other synchronously with the compression;
      a plurality of sensors on or within the cylinder, wherein each sensor is independently capable of measuring a physical or chemical characteristic of the cartilaginous tissue during application of the working radiation or the diagnostic radiation to the cartilaginous tissue;
   a feedback control system connected to the plurality of sensors, wherein the feedback control system is configured to analyze a combination of the measurements of the plurality of sensors, and to process the measurements in real time to provide feedback, wherein the measurement processing comprises:
      identifying threshold conditions that trigger a modification of treatment conditions, and
      identifying modified treatment conditions responsive to a change in a characteristic of the cartilaginous tissue following treatment as measured by the sensors; and
   a laser control unit configured to control the first and second beams of laser light, wherein the laser control unit is configured to modify one or more properties of the first or second beams of laser light based at least in part on the threshold conditions and modified treatment conditions identified by the feedback control system.

2. The device of claim 1, wherein the device is configured to be controlled by a practitioner.

3. The device of claim 1, wherein the device comprises a plurality of modular components.

4. The device of claim 3, wherein the modular components comprise a tissue connector module, fiber optic module, a sensor module, laser module, or a combination thereof.

5. The device of claim 1, wherein the sensors comprise a temperature sensor, optical sensor, optoacoustic sensor, electrical sensor, mechanical sensor, or a combination thereof.

6. The device of claim 1, wherein the physical or chemical characteristic is determined using a measurement selected from the group consisting of temperature measurements, light scattering measurements, speckle interferometry measurements, optoacoustic measurements, electrical measurements, and modulated differential scanning calorimetry measurements.

7. The device of claim 5, wherein the temperature sensor comprises a thermocouple, radiometer, or photodiode.

8. The device of claim 5, wherein the optical sensor is used for light scattering or interferometric measurements.

9. The device of claim 6, wherein the device is configured to operate by contacting at least one of the plurality of sensors with the tissue.

10. The device of claim 1, wherein the device is configured to operate in the absence of contacting at least one of the plurality of sensors with the tissue.

11. The device of claim 1, wherein the cylinder further comprises a plurality of coaxial layers.

12. The device of claim 11, wherein the plurality of layers comprise an electrically conductive layer and an electrically insulating layer.

13. The device of claim 11, wherein internal and external surfaces of the cylinder are isolated by a dielectric.

14. The device of claim 1, further comprising a mass delivery structure, wherein the mass delivery structure is capable of delivering drugs to a tissue, evacuating liquids and tissues from the tissue, or for biopsy sampling.

15. The device of claim 1, wherein the cylinder is configured to vibrate with fixed or alternating frequencies.

16. The device of claim 15, further comprising a plurality of coils, wherein the plurality of coils together is capable of producing vibrations when an electric current passes through one or more of the coils.

17. The device of claim 15, further comprising a coil and a magnet, wherein the coil and magnet together are capable of producing vibrations when an electric current passes through the coil.

18. The device of claim 1, wherein the distal end of the cylinder is sharpened to an acute angle.

19. The device of claim 11, wherein one or a plurality of the coaxial layers has chamfered forms that are capable of being adjusted prior to inserting the device into a tissue.

20. The device of claim 1, wherein the device is configured to provide optimal laser conditions prior to tissue treatment based on tissue characteristics.

21. The device of claim 1, wherein the device is configured to select an optimal tissue treatment area based on tissue characteristics.

22. The device of claim 1, wherein the sensors comprise a combination of an optical sensor for light scattering measurements, a temperature sensor, and an electrical sensor.

23. The device of claim 1, wherein the sensors comprise a combination of an optical sensor for speckle interferometry, a temperature sensor, and an optoacoustic sensor.

24. The device of claim 1, wherein the sensors comprise a combination of an optical sensor for light scattering and speckle interferometry measurements, a temperature sensor, and an optoacoustic sensor.

25. The device of claim 1, wherein the sensors comprise a combination of a photoacoustic tomography sensor and a temperature sensor.

26. The device of claim 1, further comprising a removable mandrel capable of being positioned within the lumen of the cylinder during insertion of the device into a tissue.

27. The device of claim 1, wherein the fiber optic system is removable.

* * * * *